(12) United States Patent
Chicchi

(10) Patent No.: US 10,987,521 B1
(45) Date of Patent: Apr. 27, 2021

(54) SYSTEM AND METHODS FOR TREATING BRAIN RELATED CONDITIONS WITH PHOTOBIOMODULATION THERAPY

(71) Applicant: H. O. P. E. Laser Institute, Easton, PA (US)

(72) Inventor: Mary Tonette Chicchi, Bethlehem, PA (US)

(*) Notice: Subject to any disclaimer, the term of this patent is extended or adjusted under 35 U.S.C. 154(b) by 370 days.

(21) Appl. No.: 15/786,220

(22) Filed: Oct. 17, 2017

Related U.S. Application Data

(60) Provisional application No. 62/410,224, filed on Oct. 19, 2016.

(51) Int. Cl.
 *A61N 5/06* (2006.01)
 *A61B 5/00* (2006.01)
 A61N 5/067 (2006.01)
 A61B 5/055 (2006.01)

(52) U.S. Cl.
 CPC .......... *A61N 5/0622* (2013.01); *A61B 5/4076* (2013.01); *A61N 5/0618* (2013.01); *A61B 5/055* (2013.01); *A61N 2005/067* (2013.01); *A61N 2005/0651* (2013.01); *A61N 2005/0659* (2013.01); *A61N 2005/0662* (2013.01)

(58) Field of Classification Search
 CPC .... A61B 5/4076; A61B 5/055; A61N 5/0622; A61N 5/0618; A61N 2005/0651; A61N 2005/0659; A61N 2005/0662; A61N 2005/067
 USPC ......................................................... 607/88
 See application file for complete search history.

(56) References Cited

U.S. PATENT DOCUMENTS

| | | | |
|---|---|---|---|
| 2009/0012586 A1* | 1/2009 | Kepecs ............... | A61N 5/0603 607/89 |
| 2009/0254154 A1* | 10/2009 | De Taboada ......... | A61N 5/0613 607/88 |

* cited by examiner

*Primary Examiner* — Aaron F Roane
(74) *Attorney, Agent, or Firm* — Kattina V. Barsik

(57) ABSTRACT

Photobiomodulation or low level light therapy is applied to the brain using a treatment protocol that shows improvement in treating a number of disease states and injuries of the brain. A laser probe including an LED cluster is placed perpendicular to the skull at a plurality of identified treatment points on the patient's skull for durations of 1 minute with pulsed waveforms at each location. The pattern for the treatment points varies by disease or injury state being treated. The treatment period is typically on nonconsecutive days for 6 weeks (3 times per week) or 9 weeks (2 times per week) per treatment protocol. Patients with Parkinson's disease, Alzheimer's disease, balance issues, concussions, depression, strokes, and other brain diseases or injuries have shown dramatic improvement under such treatment protocols.

13 Claims, 14 Drawing Sheets

SYSTEM AND METHODS FOR TREATING BRAIN RELATED CONDITIONS WITH PHOTOBIOMODULATION THERAPY

CROSS-REFERENCE TO RELATED APPLICATION

This patent application claims the benefit of U.S. Provisional Patent Application No. 62/410,224, filed Oct. 19, 2016, entitled "SYSTEM AND METHODS FOR TREATING BRAIN RELATED CONDITIONS WITH PHOTOBIOMODULATION THERAPY", which is incorporated by reference herein in its entirety.

BACKGROUND OF THE INVENTION

Technical Field

The invention relates to the therapeutic application of infrared light to the brain to ameliorate injury and dysfunction.

Description of Related Art

The brain is the last frontier of unknown therapy in the body. It consists of 100 billion neurons and 100 trillion synaptic connections and represents the most complicated and least understood organ of the body. Normal functioning of the brain and central nervous system ("CNS") is critical to a healthy, enjoyable and productive life. Disorders of the brain and central nervous system are among the most dreaded of diseases. Many neurological disorder such as stroke, Alzheimer's disease, and Parkinson's disease are insidious and progressive, becoming more common with increasing age. Others such as schizophrenia, depression, multiple sclerosis and epilepsy arise at younger age and can persist and progress throughout an individual's lifetime. Sudden catastrophic damage to the nervous system, such as brain trauma, infections and intoxications can also affect any individual of any age at any time. Brain disease, disorder, dysfunction, and more generally brain related ailments include all of neurology, neuropsychiatric, brain injury, brain tumor and oncology as well as congenital and hereditary issues such as Duchene Muscular Dystrophy and Downs Syndrome.

Unlike cardiovascular and metabolic disorders, where personalized health monitoring biomarkers such as blood pressure, cholesterol, and blood glucose have long become household terms, no such convenient biomarkers of brain and nervous system health exist. CT, MRI and PET scans are all diagnostic tools to non-invasively (non-surgically) look inside the body. They are all based on the fact that certain things happen to atoms in our bodies when they absorb energy (Springboard.com).

Quantitative neurophysiological assessment approaches such as positron emission tomography (PET), functional magnetic resonance imaging (fMRI) and neuropsychiatric or cognition testing involve significant operator expertise, inpatient or clinic-based testing and significant time and expense. One potential technique that may be adapted to serve a broader role as a facile biomarker of nervous system function is electroencephalography (EEG), which measures the brain's ability to generate and transmit electrical signals. However, formal lab-based EEG approaches typically require significant operator training, cumbersome equipment, and are used primarily to test for epilepsy.

Therapeutic modalities for the brain include pharmaceutical agents, biological agents and medical device therapies. Pharmaceutical agents include small molecule brain penetrating agonists and antagonists for a host of neuro receptor systems including dopaminergic, cholinergic, glutamatergic, norepinephrine, serotonergic systems. The Pharmacokinetics ("PK") must be such that the active pharmaceutical ingredient (API) not only has good PK for the body but passes the blood-brain-barrier ("BBB") design to protect and exclude foreign agents from a privileged compartment within the body. P-glycoprotein transporters typically move lots of unwanted molecules out of the BBB so drug delivery into the CNS of a human or mammalian host is often very challenging.

Biological agents include peptides, small proteins, and nucleic acids of the DNA, RNA, or PNA variety and have a host of separate and distinct challenges to become safe and effective therapeutics for brain related ailments. Medical device therapeutics strategies include TENS units, nerve stimulation, ultrasonic stimulation, hot/cold therapy, and neurobiofeedback. More recently, deep brain stimulation with implanted electrodes has been showing promise as an invasive surgical procedure.

One novel physical therapy approach that some clinicians are employing today involves the engagement of a brain injured person in treadmill exercise or stationary bike riding in order to bring the onset of headache and pain to the brain of the individual by challenging the vasculature of the brain until pain signals are loudly being sent back to the pain center within the cortex of the brain. The risks associated with this approach include embolism, increased inflammation and scar tissue and therefore may not be the best approach to rehabilitate the brain. This new physical therapy is both painful, time consuming, costly and has its own set of risks to the patient.

Cold laser therapy, otherwise known as low level laser therapy and photobiomodulation, is non-invasive, painless and has no known side effects. Various published protocols for cold laser therapy have been utilized on various brain related conditions including the protocol described by Xuan, W., Vatansever F., January, 2013, PLOS, Transcranial Low-Level Laser Therapy Improves Neurological Performance in Traumatic Brain Injury in Mice. Other articles supporting the continuation of research and the positive influence of low level light therapy are noted in the following articles: Hashmi, J., 2010, National Institute of Health, Role of Low-Level Laser Therapy in Neurorehabilitation; Gonzalez, F., Barrett, D., Frontier, System Neuroscience Journal, March 2014, Frontiers/Augmentation of Cognitive Brain Function with Transcranial Lasers, Augmentation of cognitive brain functions with transcranial lasers, Low-level laser therapy for traumatic brain injury in mice increases brain derived neurotrophic factor and synaptogenesis; Low level laser therapy for traumatic brain injury. It should be noted that rodent and non-human preclinical animal models have a poor translational predictive validity and thus animal research, although interesting from a mechanistic perspective, does not typically guide the clinician in what to do in a human brain therapy context.

Moreover, the published cold laser therapy literature teaches one to apply infrared light to the brain. Some papers teach continuous stimulation of neural tissue (Chung, H., 2012, National Institute of Health, The Nuts and Bolts of Low-level Laser (Light) Therapy) whereas others teach to use pulsed IR light (Hashmi, J. 2010, National Institute of Health, Effect of Pulsing in Low-Level Light Therapy). The published literature is all over the place with IR frequency including those in the 810-850 nm range (Ando, T. Xuan, W. 2011, National Institute of Health, Comparison of Therapeutic Effects between Pulsed and Continuous Wave 810-nm Wavelength Laser Irradiation for Traumatic Brain Injury in Mice) as well as longer wavelengths such as 1064 nm IR light (Lins, E., Oliveira, C., Oct. 13, 2013, National Institute of Health, A Novel 785-nm Laser Diode-Based System for Standardization of Cell Culture Irradiation). The pulse rate frequency in publications is suggested to range from 2.5 Hz to 1.25 KHz (Chang, W., Wu, J., April 2014, National Institute of Health, Therapeutic outcomes of low-level laser therapy for closed bone fracture in the human wrist and hand) and a 10 Hz pulse rate is suggested for treatment. Duration of time at any given spatial location on the skull outside the brain is also all over the place. Xuan, W., Vatansever F., January, 2013, PLOS, Transcranial Low-Level Laser Therapy Improves Neurological Performance in Traumatic Brain Injury in Mice: Effect of Treatment Repetition Regimen describes one of many studies that show individual treatment parameters with little to no conformity for a treatment regimen. Spatial locations vary from condition to condition and include trans nasal access for the frontal lobe for AD (Queslati, A. Lovisa, B. October 2015, National Institute of Health, Intranasal Light Therapy Devices), parietal lobe stimulation for Parkinson's, and cerebral cortex in back (occipital) for balance related therapy (Queslati, A. Lovisa, B., et al., October 2015, National Institute of Health, Photobiomodulation Suppresses Alpha-Synuclein-Induced Toxicity in an AAV-Based Rat Genetic Model of Parkinson's Disease). Additionally, the literature teaches 4-5 days of treatment in a row (Xuan, w., Vatansever F., January, 2013, PLOS, Transcranial Low-Level Laser Therapy Improves Neurological Performance in Traumatic Brain Injury in Mice: Effect of Treatment Repetition Regimen). Protocols that are highly effective range from 3-7 days to 1 to 12 weeks depending on a multitude of parameters like condition, progression of the disease and power and duty cycle of laser treatment.

Alternate and innovative therapeutic approaches are needed to provide safe and effective therapy for the brain and its brain related ailments. Cold laser therapy offers an exciting opportunity to provide safe and effective therapy for brain related ailments. The invention provides, among other things, treatment protocols for use of cold laser therapy to treat brain injuries and disorders.

SUMMARY OF THE INVENTION

The invention addresses the above and other needs in the art by providing a method of treating brain disease and/or brain injuries comprising determining a treatment protocol for a subject having a particular brain disease and/or brain injury and then applying the treatment protocol to the subject. In exemplary embodiments, the treatment protocol includes a plurality of treatments, each treatment including application of light to the brain at a light frequency and duration of application of light at respective positions in a pattern on the patient's skull in dependence upon the particular brain disease and/or brain injury being treated. For each treatment, the operator applies a light probe to the subject's skull at respective positions on the patient's skull in the pattern that is predetermined to provide effective treatment for the particular brain disease and/or brain injury. Light is then applied at the treatment frequency for the predetermined period of time at each treatment position.

Different treatment protocols are used to treat different brain diseases or injuries. For example, the pattern may be a 9 point treatment pattern including a point on the center top of the subject's head, left and right side occipital positions behind the left and right ears, left and right sides of the skull straight up from a center of each ear of the subject, left and right sides of the forehead, and on the forehead above the left and right eyes. Such a 9 point treatment pattern is used in treatment of concussion, traumatic brain injury, depression, Duchene Muscular Dystrophy, ADD, ADHD, central auditory processing disorder, autism, Tourette's syndrome, post-traumatic stress disorder, stroke, neuropathy, chronic fatigue, Down's syndrome, chronic traumatic encephalopathy, circulation, cerebral palsy, amblyopia, mitochondrial disorders, behavioral disorders, or lymphedema, for example.

On the other hand, the pattern may be an 11 point treatment pattern including a point on the center top of the subject's head, left and right side occipital positions behind the left and right ears, left and right sides of the skull straight up from a center of each ear of the subject, left and right sides of the forehead, on the forehead above the left and right eyes, and on the left and right sides of the skull between the point on the center top of the subject's head and points on the left and right sides of the skull straight up from the center of each ear of the subject. Such an 11 point pattern is used in the treatment of Parkinson's disease, for example.

Alternatively, the pattern may be an 11 point treatment pattern including a point on the center top of the subject's head, left and right side occipital positions behind the left and right ears, left and right sides of the skull straight up from a center of each ear of the subject, left and right sides of the forehead, on the forehead above the left and right eyes, and on the left and right sides of the skull between the bridge of the subject's nose and the orbit or eye socket. Such an 11 point pattern is used in the treatment of Alzheimer's disease.

In another embodiment, the pattern may be an 11 point treatment pattern including a point on the center top of the subject's head, left and right side occipital positions behind the left and right ears, left and right sides of the skull straight up from a center of each ear of the subject, left and right sides of the forehead, on the forehead above the left and right eyes, and at the base of the skull on the occipital ridge adjacent to the left and right sides of the spine. Such an 11 point pattern is used in the treatment of balance disorders.

In still another embodiment, the pattern may be an 11 point treatment pattern including a point on the center top of the subject's head, left and right side occipital positions behind the left and right ears, left and right sides of the skull straight up from a center of each ear of the subject, left and right sides of the forehead, on the forehead above the left and right eyes, and over the left and right ear canals. Such an 11 point pattern is used in the treatment of tinnitus.

In yet another embodiment, the pattern may be a 13 point treatment pattern including a point on the center top of the subject's head, left and right side occipital positions behind the left and right ears, left and right sides of the skull straight up from a center of each ear of the subject, left and right sides of the forehead, on the forehead above the left and right eyes, over the left and right ear canals, and at the base of the skull on the occipital ridge adjacent to the left and right sides of the spine. Such a 13 point pattern is used in the treatment of tinnitus with traumatic brain injury.

In the respective treatment protocols, the light preferably has the following characteristics: a frequency of 2.5 Hz, 10 Hz, or 1.25 kHz the form of an alternating square wave having a wavelength of approximately 810 nm, and a continuous mode or a pulsed mode. In exemplary treatment protocols, the light is applied perpendicular to the brain for 1 minute at each treatment position. An exemplary treatment protocol may comprise 18 treatments 3 times a week for 6 weeks or 2 times a week for 9 weeks on nonconsecutive days.

In an alternative embodiment, the light probes are arranged at the respective treatment positions within a helmet worn by the patient. These and other modifications to the exemplary treatment protocol will become apparent from the following detailed description of the respective exemplary embodiments.

BRIEF DESCRIPTION OF THE DRAWINGS

Embodiments of the invention can be better understood with reference to the following drawings, of which.

DETAILED DESCRIPTION OF THE INVENTION

Figure 1:
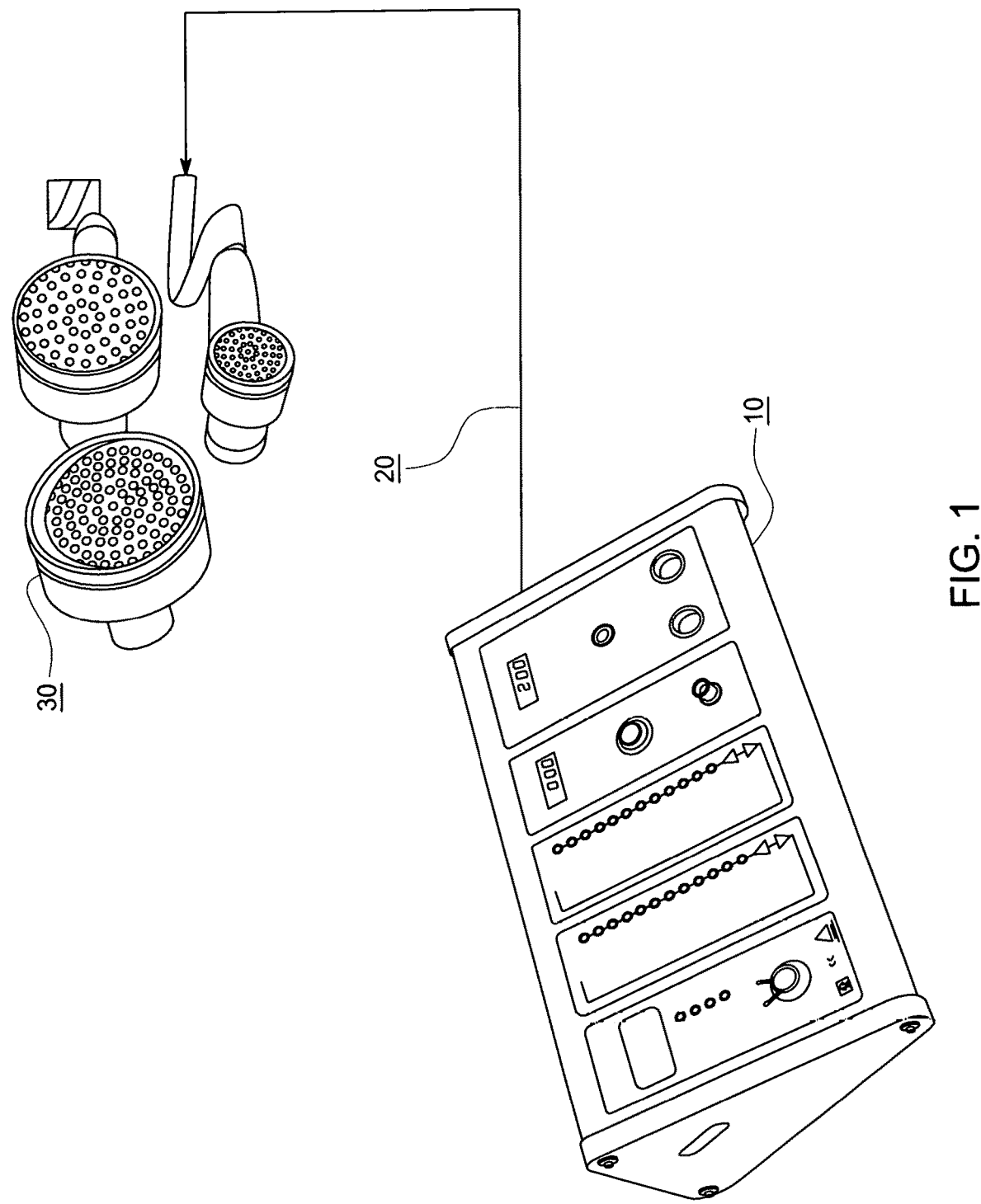
FIG. 1 is an illustration of an infrared laser light emitter unit, LEDs, and connection cord used for treatment.

Certain specific details are set forth in the following description with respect to FIGS. 1-13 to provide a thorough understanding of various embodiments of the invention. Certain well-known details are not set forth in the following disclosure, however, to avoid unnecessarily obscuring the various embodiments of the invention. Those of ordinary skill in the relevant art will understand that they can practice other embodiments of the invention without one or more of the details described below. Also, while various methods are described with reference to steps and sequences in the following disclosure, the description is intended to provide a clear implementation of embodiments of the invention, and the steps and sequences of steps should not be taken as required to practice the invention.

Definitions

By "mammalian host or human" we mean to include, without limitation, all mammals in the biological zoology all the way from the rodent to the top of the food chain human (*Homo sapiens*). This would include all transgender and novel gender independent variants of mammals including humans.

By "cold laser therapy" or "low level light therapy" or "photobiomodulation" we mean to include, without limitation, equivalent terms that encompass the use of near infrared light emission directed at the neural tissue of the human or mammalian host brain tissue in order to induce an therapeutic response to the stimulation of the tissues with the IR light emission.

A "medical therapy" as used herein is intended to encompass any form of therapy with potential medical effect, including, without limitation, any pharmaceutical agent or treatment, compounds, biologics, medical device therapy, exercise, biofeedback or combinations thereof.

An "electronic system" as used herein is intended to encompass, without limitation, hardware, software, firmware, analog circuits, DC-coupled or AC-coupled circuits, digital circuits, FPGA, ASICS, visual displays, audio transducers, temperature transducers, olfactory and odor generators, or any combination of the above.

By "biomarker" we mean an objective measure of a biological or physiological function or process.

By "biomarker features or metrics" we mean a variable, biomarker, metric or feature which characterizes some aspect of the raw underlying time series data. These terms are equivalent for a biomarker as an objective measure and can be used interchangeably.

By "non-invasively" we mean lacking the need to penetrate the skin or tissue of a human subject.

By "diagnosis" we mean any one of the multiple intended use of a diagnostic including to classify subjects in categorical groups, to aid in the diagnosis when used with other additional information, to screen at a high level where no a priori reason exists, to be used as a prognostic marker, to be used as a disease or injury progression marker, to be used as a treatment response marker or even as a treatment monitoring endpoint.

By "69 cluster probe" we mean a LED laser probe that emits IR light consisting of LED diodes only.

By "laser probe" we mean LED/LASER diode combination probe that emits IR light with both diodes.

By "cold laser" we mean a device that falls into the 3b laser class.

By "side effects" we mean any adverse side effects or conditions that would make the subject uncomfortable or cause additional pain. Experiencing thirst or tiredness would not constitute a side effect.

Theory Behind Cold Laser Light Therapy

A review of the literature suggests that photobiomodulation ("PBM") or low level light therapy ("LLLT") or cold laser light therapy works by stimulating mitochondrial production leading to enhanced cell function, repairing of damaged tissue and enhanced blood flow. There are numerous studies citing the effects of PBM. PBM increases ATP, increases neuro-genesis, and helps eliminate scar tissue.

LLLT is explained as exposing cells or tissue to low levels of red and near infrared (NIR) light (Chung, H., 2012, National Institute of Health, The Nuts and Bolts of Low-Level Laser Therapy). Although LLLT is now used to treat a variety of issues, controversy still surrounds the treatment primarily due to two principle reasons. The biomechanics of LLLT is poorly understood and there is a vast amount of parameters that affect the use of LLLT such as wavelength, power density, pulse structure, timing and location.

The amplitude of the light energy determines its brightness and the wavelength determines its color, within the spectrum of colors of the rainbow from violet to red, and the angle of its electric field vibration determines its polarization. Photons are particles of energy that move to the speed of light therefore the number of photons determines brightness and the energy (proportional to frequency and inversely proportional to wavelength) in the photon determines its color. The word laser stands for Light Amplification by Stimulated Emission of Radiation. Lasers use very small beams that concentrate power at high energy density. A coherent beam implies that the light output is in the form of a polarized wave at a single frequency (and thus wavelength).

The precise biophysical and biochemical mechanism underlying the therapeutic effects of LLLT are not well established. It appears the LLLT has a wide range of effects at the molecular, cellular, and tissue levels, including but not limited to modulation of reactive oxygen species (ROS) and induction of transcription factors which in turn increase protein synthesis that triggers increased cell proliferation. Migration, modulation in cytokines, growth factors and inflammatory mediators and increased tissue oxygenation are all positive changes that occur with LLLT (Hamblin, 2011, Harvard Medical Journal Department of Dermatology, Mechanisms of low level light therapy).

The systems and methods of the present invention comprise light sources, light pipes and application devices which interface to the skull of a host mammalian brain. It is often necessary to insure the integrity and good calibration of opto-electronic equipment. Often trained operators and engineers conduct detailed and extensive calibration procedures with scientific instruments traceable to a reference standard like a National Institutes of Standards and Testing (NIST) traceable standard. Certificates of Analysis often link a local calibration to a known reference standard. The same needs to be true for optoelectronic infrared light delivery systems and methods. Unfortunately, often problems emerge like an intermittent contact or a complete disruption of an electrical conductor or contact. Often electrical components can fail and an operator or subject may not know that everything is not working.

A solution to these problems includes a daily calibration and quality control system which is a part of the hardware/software system to deliver therapeutic infrared light. Typically, therapeutic infrared light systems include a light source, either gas, solid state resonator rod, or semiconductor diode, connected by a chain of optics or an optical fiber to a movable light delivery head unit which is applied to the skull of a mammalian host or human.

There are approximately 5.3 million traumatic brain injury ("TBI") and concussions currently in the United States. Although we have made great strides for prevention by offering new technologically advanced equipment and state of the art analysis for detection, there is very little development in treatment of the conditions. Rest, disengagement from everyday life and a host of pain and antidepressants are the only therapeutic tools currently in use.

Overview of Cold Laser Light Therapy Systems

FIG. 1 is an illustration of an infrared laser light emitter unit, LEDs, and connection cord used for treatment. FIG. 1 illustrates a basic IR emitting unit 10 with a light board establishing length of time of treatment and frequency (in Hz) of treatment. The two open ports on the right side of the unit 10 are for the cord or light pipes 20 which connect the unit 10 to the laser probes 30. Although only one probe 30 is shown as connected to unit 10, two probes may be connected to unit 10 though typically only one laser probe 30 functions at a time. The laser probes 30 may include a 69 LED cluster, a 104 LED Cluster and a 9 LED/Laser probe. As illustrated, the unit 10 has a key start located on the left side.

Figure 2:
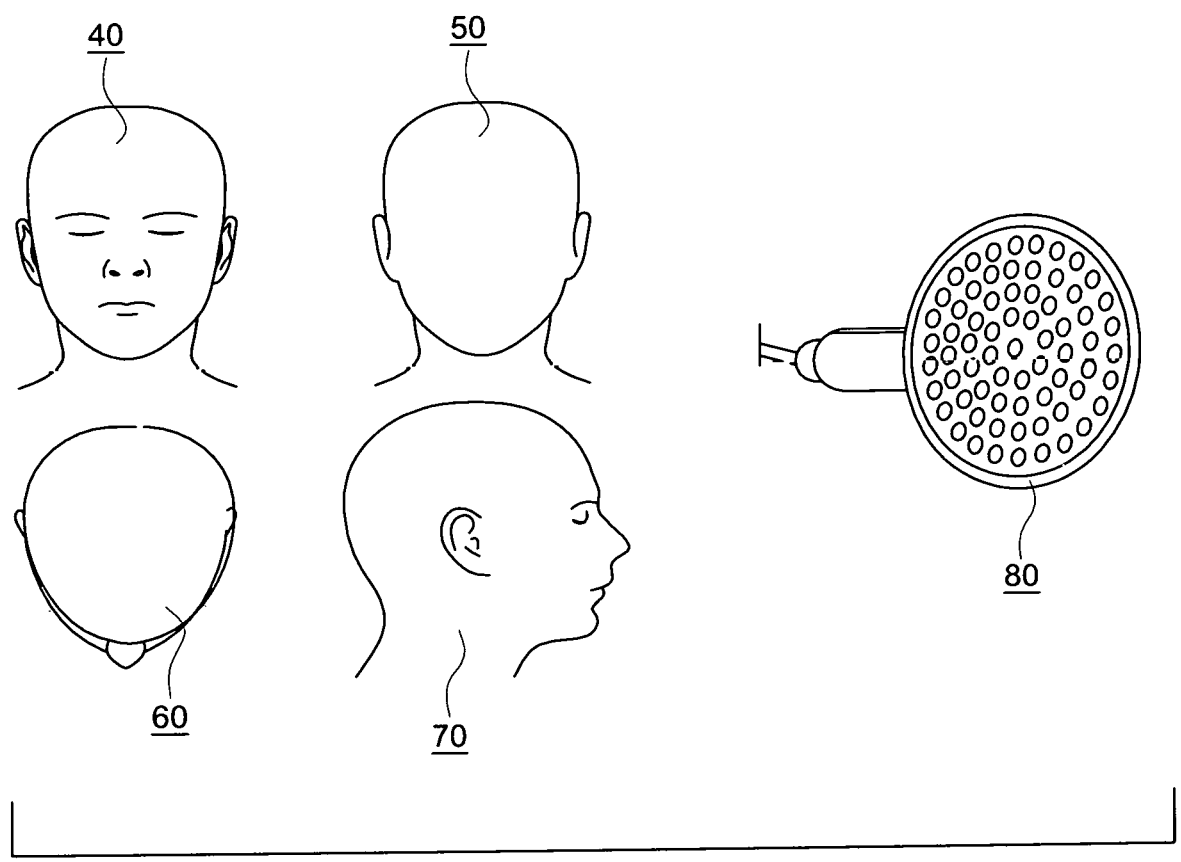
FIG. 2 is a schematic diagram illustrating the four views of the human head and skull along with a detailed view of a 69 cluster LED head.

FIG. 2 includes four views of a human brain from the front 40, back 50, top 60 and side 70 as well as a close up view of the 69 LED probe 80. It will be appreciated by those skilled in the art that any treatment sites that are located on the right side view will be consistent with the left side view as well. Placements for the laser probes 30 during treatment will be described below for different treatment protocols.

Figure 3:
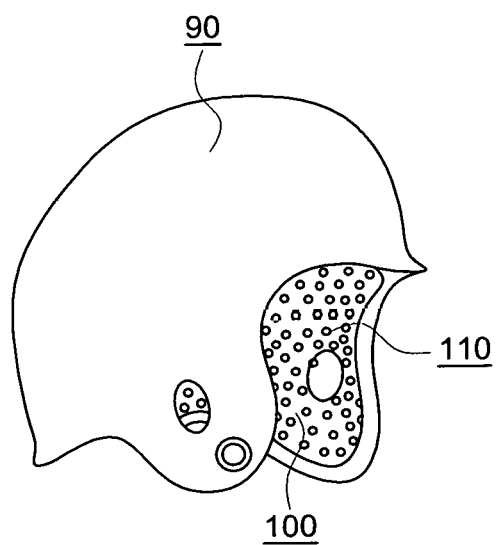
FIG. 3 is a schematic diagram illustrating the IR laser lights incorporated into a helmet configuration.

FIG. 3 is a rough illustration of an embodiment of an LED helmet 90 with LEDs 100 installed on the inside of the helmet at various spatial locations 110 around the brain.

Figure 4:
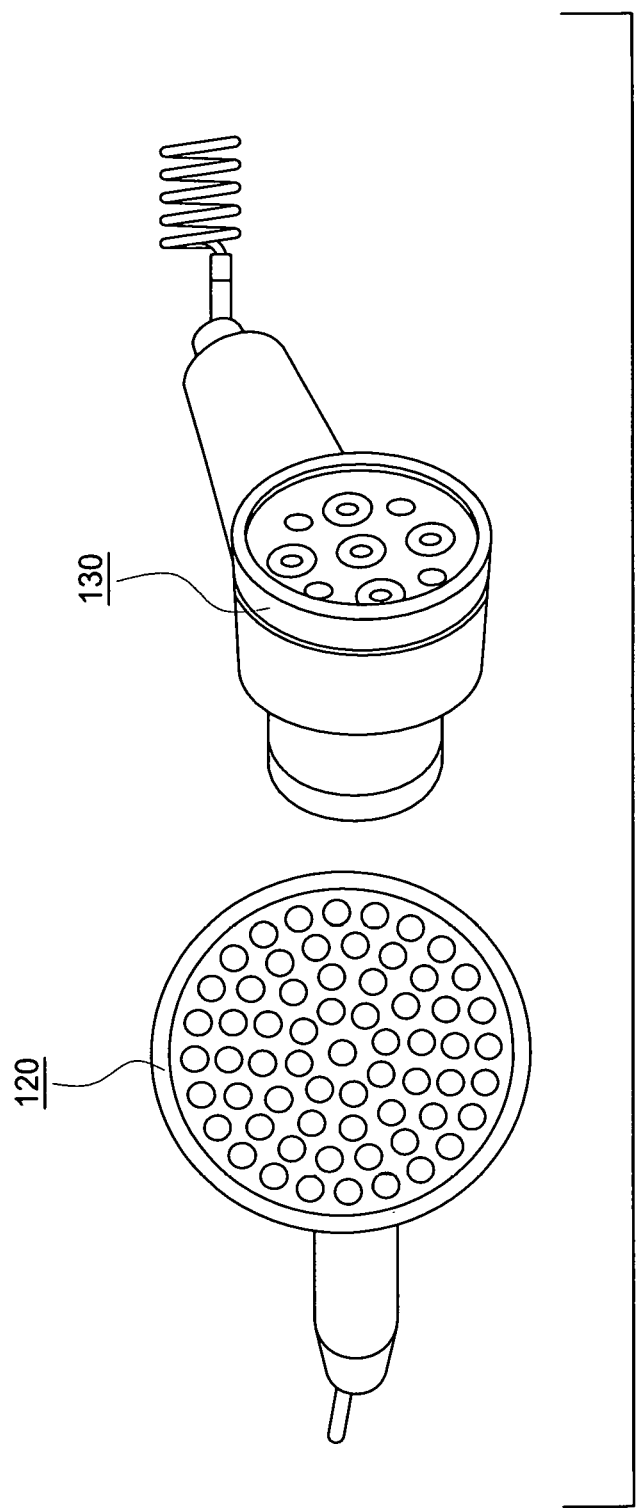
FIG. 4 is schematic diagram illustrating a 69 cluster probe versus a 9 cluster probe IR laser light emitter configuration.

FIG. 4 illustrates a 69 LED probe 120 and a 9 cluster laser probe 130 to facilitate comparison.

As will be described in more detail below, the cold laser therapy system illustrated in FIGS. 1-4 may be used in accordance with exemplary treatment protocols to address a variety of brain injuries and disorders.

The IR Laser Therapy Experimental Control Parameters

The cold laser protocol system has a pulsed wave which is used for all treatment protocols. The continuous wave setting is only used with the LED/Laser probe for analgesic effects. The pulsed wave therapy gives the benefits listed for encouraged cell function, repair and replacement.

Mode of stimulation—continuous versus pulsed infrared ("IR") light. LED infrared lasers either emit their output continuously or intermittently in a pulsed but well defined period fashion. This is referred to as either continuous mode or pulsed mode.

Laser head cluster design/configuration. The 69 cluster is an LED probe with a wider more shallow cellular reach than the 9 LED/Laser probe. The 9 LED/Laser probe penetrates more deeply due to its tight concentrated beam. LED/Laser probes are typically used for analgesic effects. The 9 cluster LED/Laser probe is produced with both diodes so it may be utilized for either treatment. Both the LED and the LED/Laser probe have a combination of the output from two different laser diodes, one with emission at 660 nm and the other with 810 nm emission. The 660 nm falls within the visible red light emission. The 810 nm is the most widely used wavelength and falls outside the visible spectrum of the human eye. Studies show 810 nm is absorbed by the cytochrome oxidase and helps eliminate nitric oxide ("NO") which reduces oxidative stress and the generation of reactive oxygen species ("ROS"). 810 nm light stimulates the mitochondria of the cells thus increasing ATP production at the cellular level. In contrast, when a more shallow but larger surface area needs to be treated, a 69 LED probe or larger can be used. When treatments need to be deeper and the need for analgesic effects are required the 9 LED/Laser probe is used.

Wavelength of light (nm). The wavelength of light is typically calibrated at 810 nm. This wavelength has been shown in studies to be the most reactive at cellular repair and the stimulation of ATP. Although there are other wavelengths that have shown benefit, the 810 nm laser line is considered the gold standard for addressing healing, neurological, and physical benefits.

Pulse Frequency. The pulse rate frequency (in Hz) is the rate of delivery and determines how fast photons are delivered to the cell through treatment. If a larger amount of photons are desired, higher frequencies (in Hz) are used so that more photons will be delivered. The frequency is selected in accordance with the purpose of the treatment. For example, when treating brain cells, new research is suggesting a 10 Hz delivery system. That has changed from a few years ago which stated that 1.25 KHz was the best repetition rate of delivery of infrared light for brain tissue.

Stimulation time per site on the skull is measured in minutes or seconds of treatment. Most of the protocols are based on minute intervals. The prior art has shown that overstimulation causes the cell's function to be slowed or shut down.

The Treatment Protocol of the Present Invention

The literature guides that each physical location or site on the skull within a protocol is dispersed at 1 minute intervals. Additional points of treatment are added before increased time at a single point. Research suggests there is a biphasic dose response. The research further dictates that if cells are over stimulated for too long they will shut down and the condition may actually become worse over time. On the other hand, if patients receive less that the needed dosage, they may experience some benefit but the maximum level of benefit will not be achieved. The protocols are key to establishing the proper amount of IR light to offer the maximum benefit. Power density of light (mW/cm2) is typically defined through the formula of light power/surface area.

The pattern of the stimulation is important to the repair of cognitive function. The diagonal pattern that starts at the occipital and then moves onto the parietal lobe stimulates the left and right sides of the brain, encouraging impulses from each side to fire at the same time which stimulates more brain activity. The pattern causes neuron stimulation to the areas of the brain controlling eye hand coordination. The angle of the LED or Laser probe is also important to the success of the treatment. The LED or Laser probe must be perpendicular to the desired area of treatment. It is also important to treat the entire brain area. Although exact location of trauma may be known, the scattering effect of the IR light when it hits the skull goes randomly to different areas of the brain. The efficacy of treatment is thus dependent on use of the proper protocol.

Figure 5:
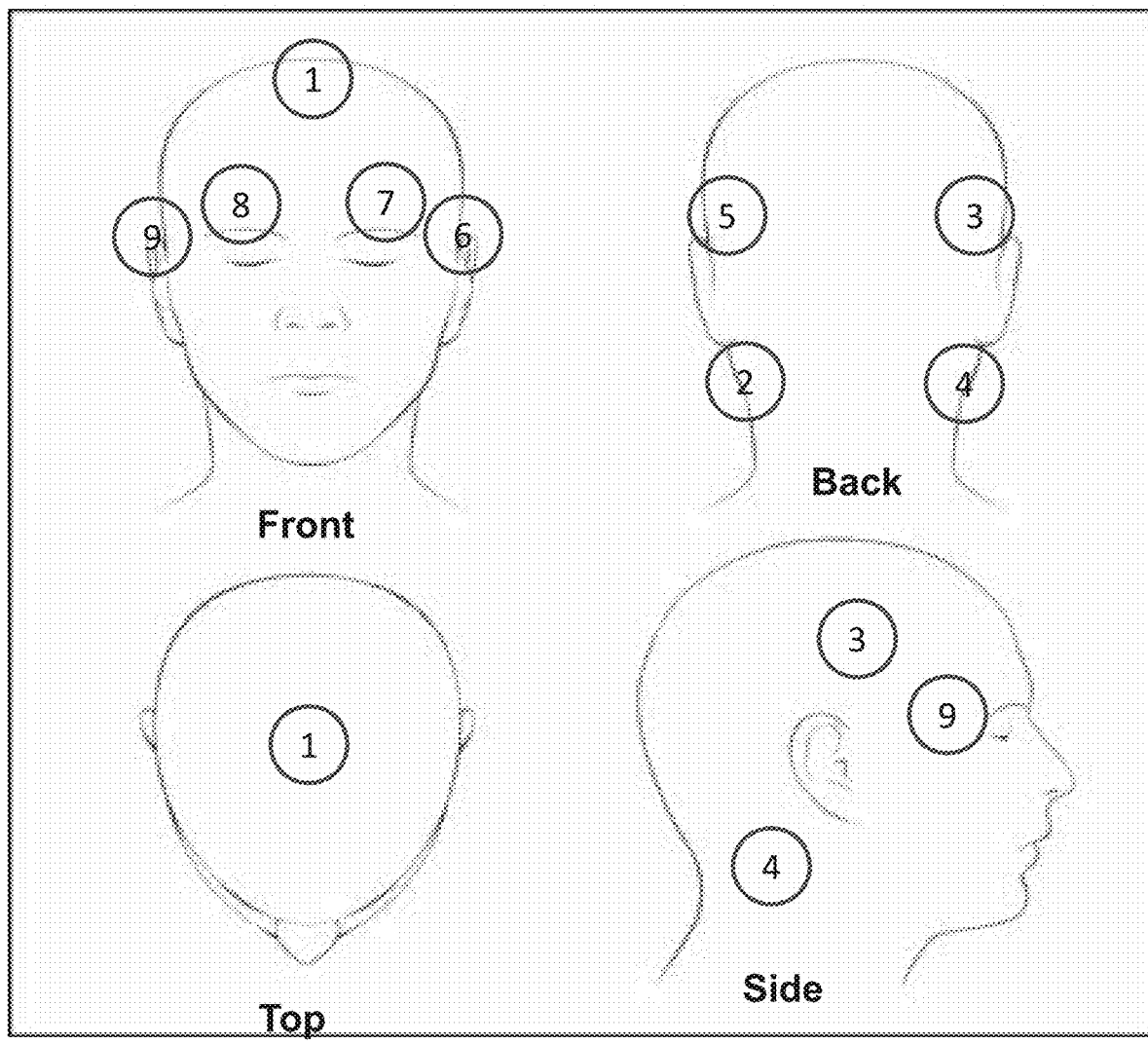
FIG. 5 is a graphical diagram of four views of the skull illustrating the locations and order of treatment for a 9 point therapeutic basic cognitive treatment for treating learning disabilities and neurological conditions in an exemplary embodiment.

The periodicity of clinical treatment to the human brain is also important to the outcome of the treatment protocol. The system and methods of the present invention include treatment typically three (3) times a week in order to build the level of ATP in the mitochondria to sustain a high level of recovery. An example of this would be Monday, Wednesday and Friday treatment. If 2 times a week is established with the patient, then the treatment times are extended to 9 weeks instead of 6, ex. Tuesday and Thursday so that a total of 18 treatments are conducted. One skilled in the art will realize that shorter treatment regimens and longer regimes may be necessary on a case by case basis or based on other clinical circumstances but are still within the scope of the treatment protocols of the present invention. 18 treatments is the basic neurological protocol for almost every neurological condition. However, treatments on 2 or 3 consecutive days is not the most beneficial. The overstimulation in the short term of 3 consecutive days and then ATP loss over the long time period between sessions is not conducive for optimal results. Although some research states that 3, 5 and 7 consecutive days are sufficient, the inventors have not found this to be true in human cases. The research is mostly conducted on rodents. Brain stimulation patterns for effective therapy The basic cognitive pattern of 9 points of treatment has shown to be effective in all neurological conditions. There have been points added to some of the more progressive diseases, but even they are developed around the 9 treatment points as illustrated in FIG. 5. Note that each point on the skull is numbered in sequential order and where visible from more than one view, it is noted in at least one view but sometimes in 2 views.

FIG. 5 is a graphical diagram of four views of the skull illustrating the locations and order of treatment for a 9 point therapeutic basic cognitive treatment for treating learning disabilities and neurological conditions in an exemplary embodiment. The pattern and location of the LED probe is illustrated where each circle represents the LED probe at 2.5 Hz for a duration of 1 minute. The LED probe is placed directly on the skull perpendicular to the treatment area. After the unit is programed for the time and treatment frequency (in Hz), the treatment proceeds with each numbered point, starting at point 1 and ending at point 9.

Figure 6A:
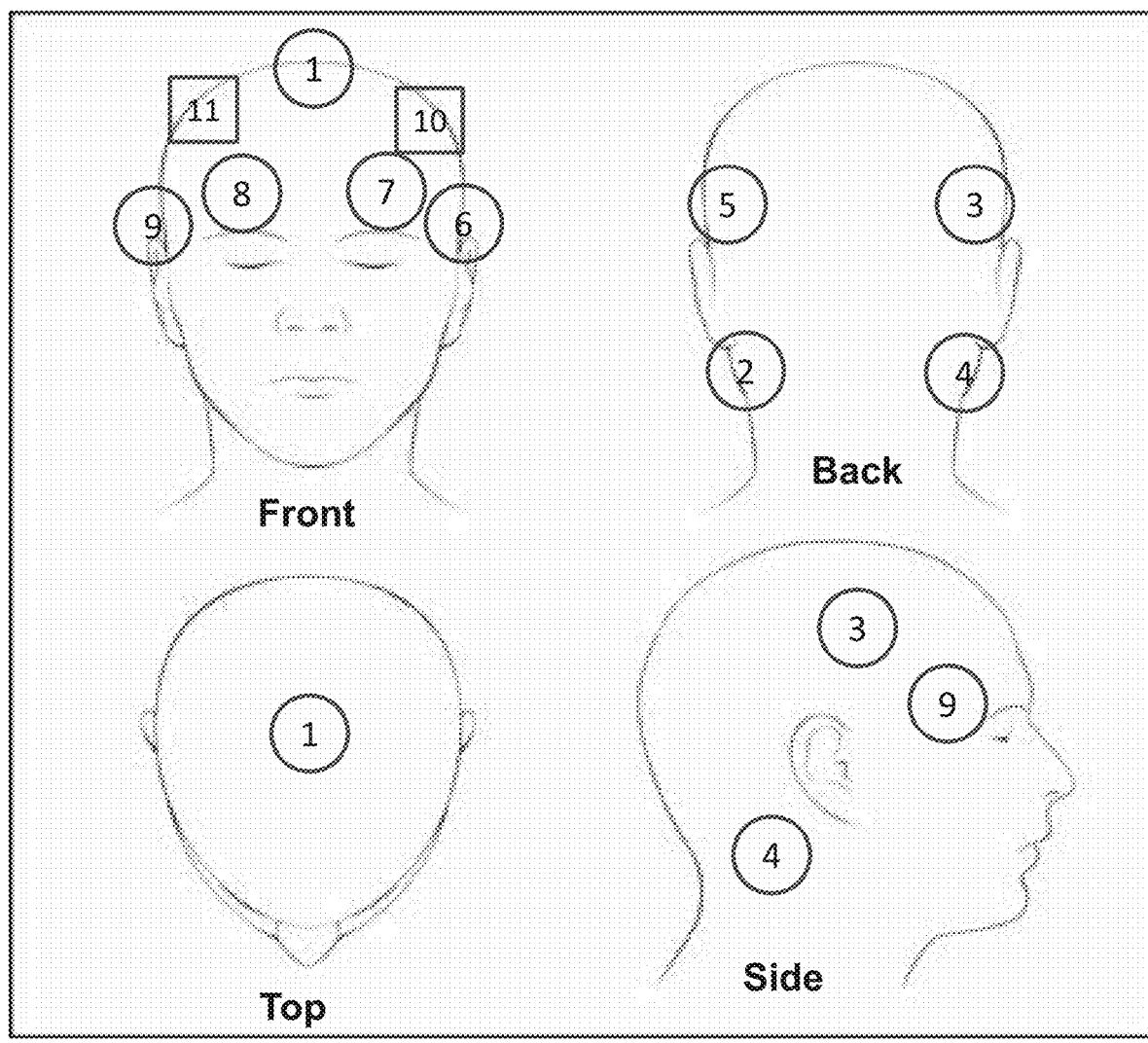
FIG. 6A is a graphical diagram of four views of the skull illustrating the locations and order of treatment for an 11 point therapeutic treatment for Parkinson's disease.

FIG. 6A illustrates an 11 point Parkinson treatment protocol that has two additional points added to the 9 point protocol shown in FIG. 5. The left and right side of the brain between 3 and 8 and 5 and 7 are given extra treatment to help stimulate the production of dopamine.

The 11 point treatment protocol for Alzheimer's disease shown in FIG. 6B is again the basic 9 point treatment protocol with 2 additional points at the ocular ridge closest to the bridge of the nose. Research shows the frontal lobe of the brain is the most effected by Alzheimer's. Directly using the soft tissue above the eye gives a more direct treatment to the frontal lobe with the infrared laser light.

Figure 6B:
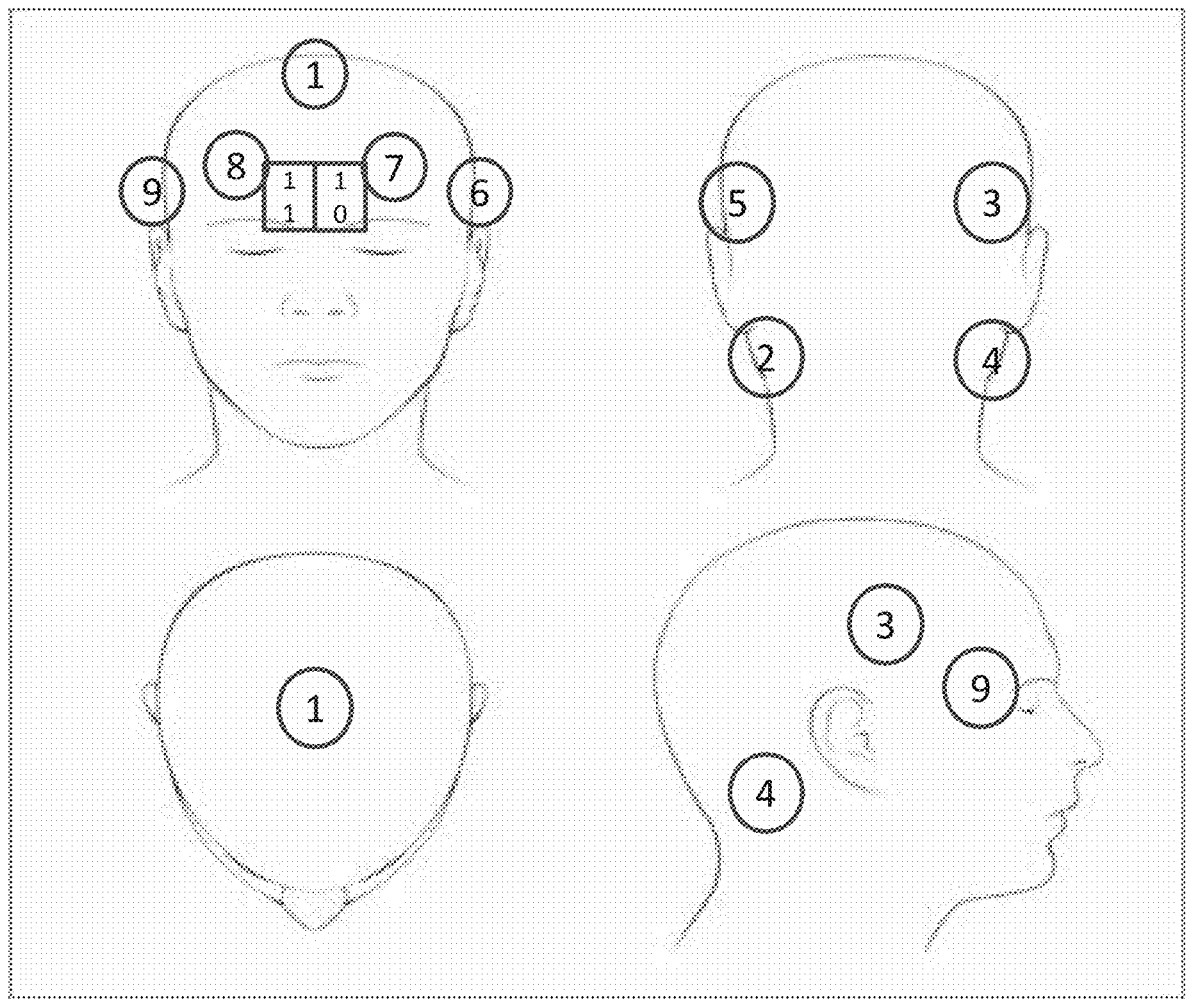
FIG. 6B is a graphical diagram of four views of the skull illustrating the locations and order of treatment for an 11 point therapeutic treatment for Alzheimer's disease.
Figure 6C:
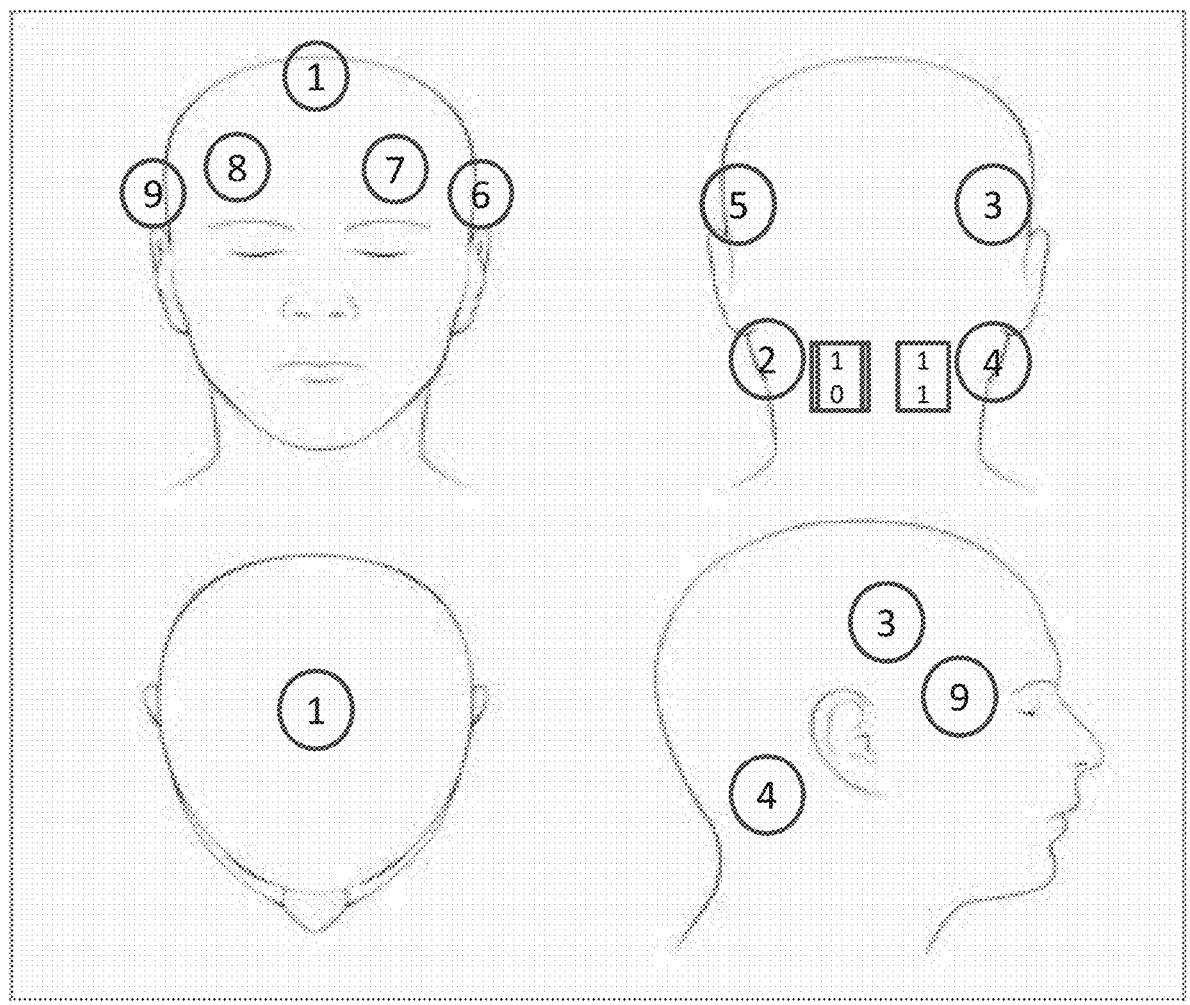
FIG. 6C is a graphical diagram of four views of the skull illustrating the locations and order of treatment for an 11 point therapeutic treatment for balance and vestibular issues.

The balance or vestibular issues that are associated sometimes with stroke, TBI, Parkinson's and Alzheimer's are treated with 2 additional points at the base of the occipital bone, just left and right of the spinal column after the initial 9 point pattern is completed, as shown in FIG. 6C. The pattern helps stimulate the area of the brain responsible for balance and the tissue in this area allows for a more direct delivery of treatment without the scattering due to the skull.

Figure 7:
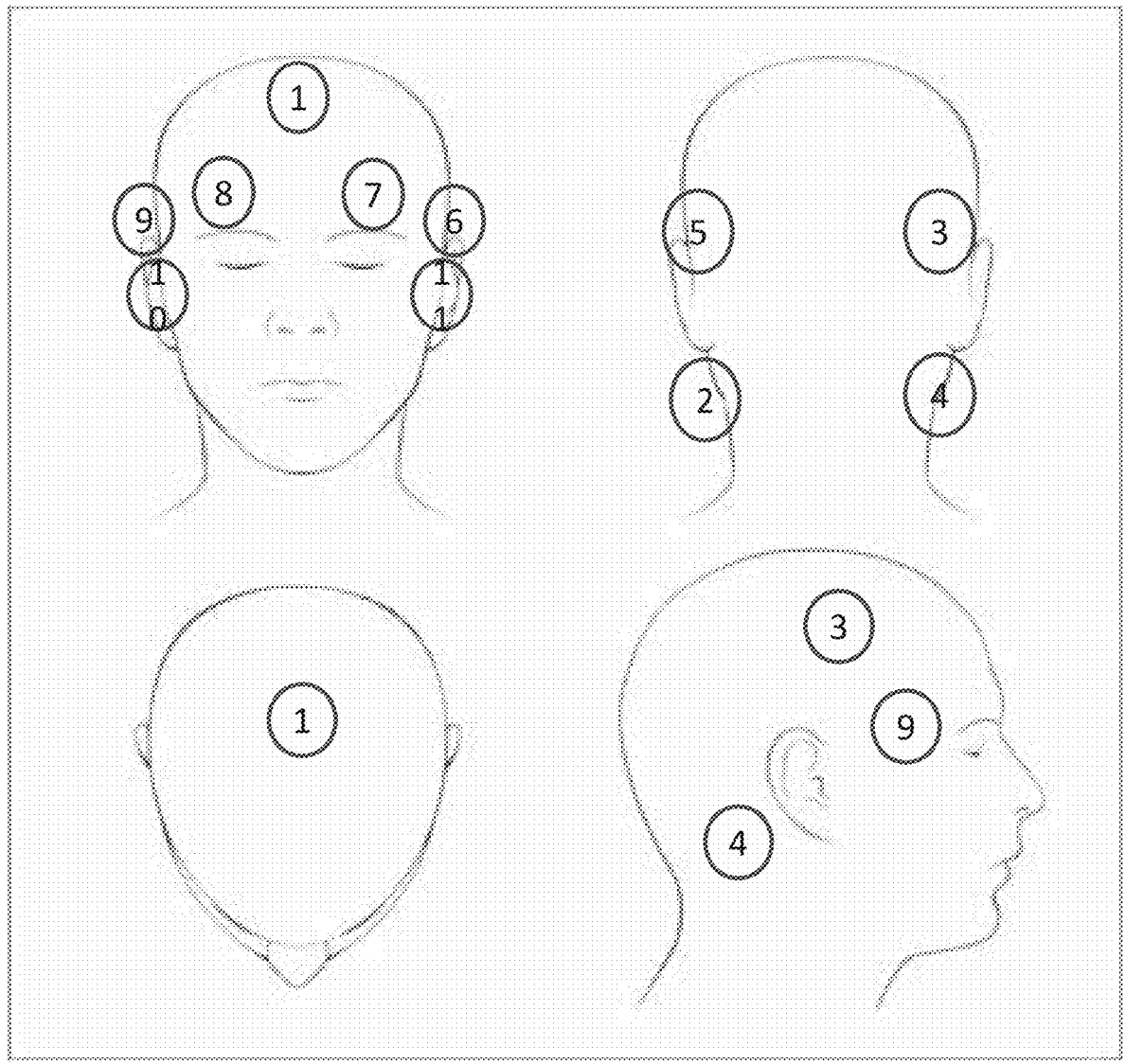
FIG. 7 is a graphical diagram of four views of the skull illustrating the locations and order of treatment for an 11 point therapeutic treatment for Tinnitus.

The 11 point pattern for Tinnitus is shown in FIG. 7 where one sees the basic 9 point pattern with 2 additional points placed directly on the ear canal using the 69 cluster. Stimulating the ear canal helps address the issues of inflammation and scar tissue.

Figure 8:
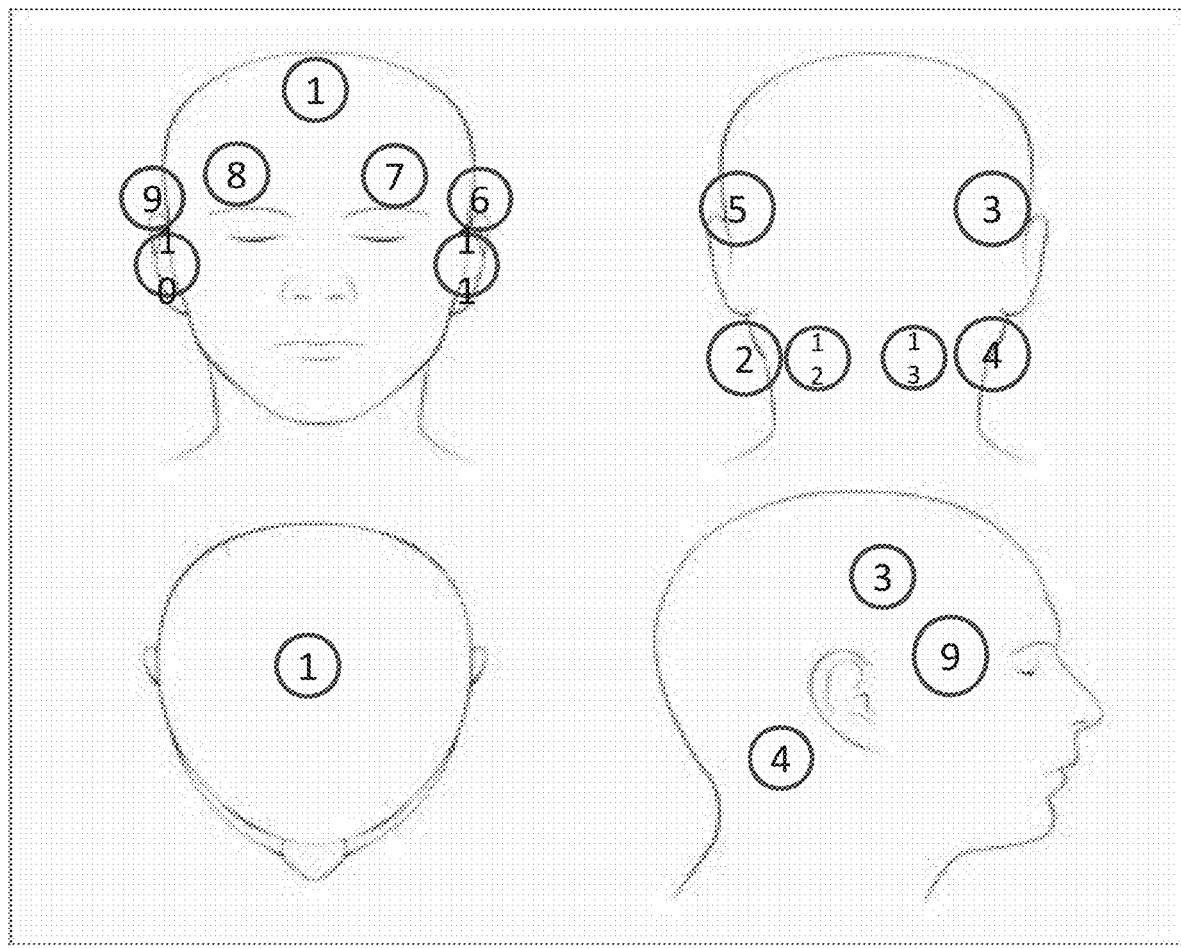
FIG. 8 is a graphical diagram of four views of the skull illustrating the locations and order of treatment for a 13 point therapeutic treatment for Tinnitus with TBI.

The 13 point pattern for Tinnitus with TBI is shown in FIG. 8 where one sees that the basic 9 points with 4 additional points, 2 of the points are at the base of the occipital one on each side of the spine as well as 2 points over the ear canal. Stimulating the ear canal helps address the issues of inflammation and scar tissue. The additional points at the occipital stimulate the brain stem.

Duration of Light Stimulation and Pulse Rate Frequency

Figure 9:
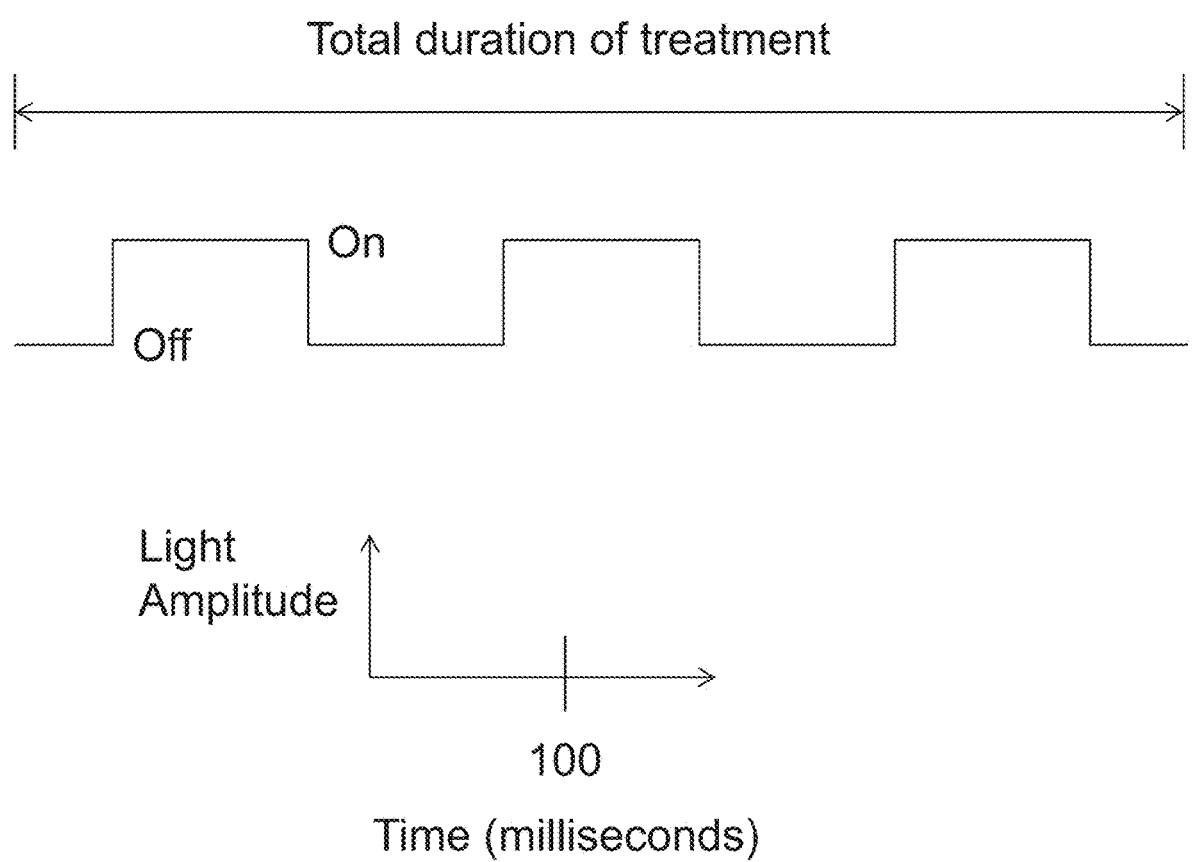
FIG. 9 represents the duration of treatment as well as pulse rate frequency where all treatment locations are given one minute of treatment; the frequency is placed at 2.5 Hz and all neurological frequencies are either 2.5 Hz, 10 Hz, or 1.25 KHz depending on patient progress.
Figure 10:
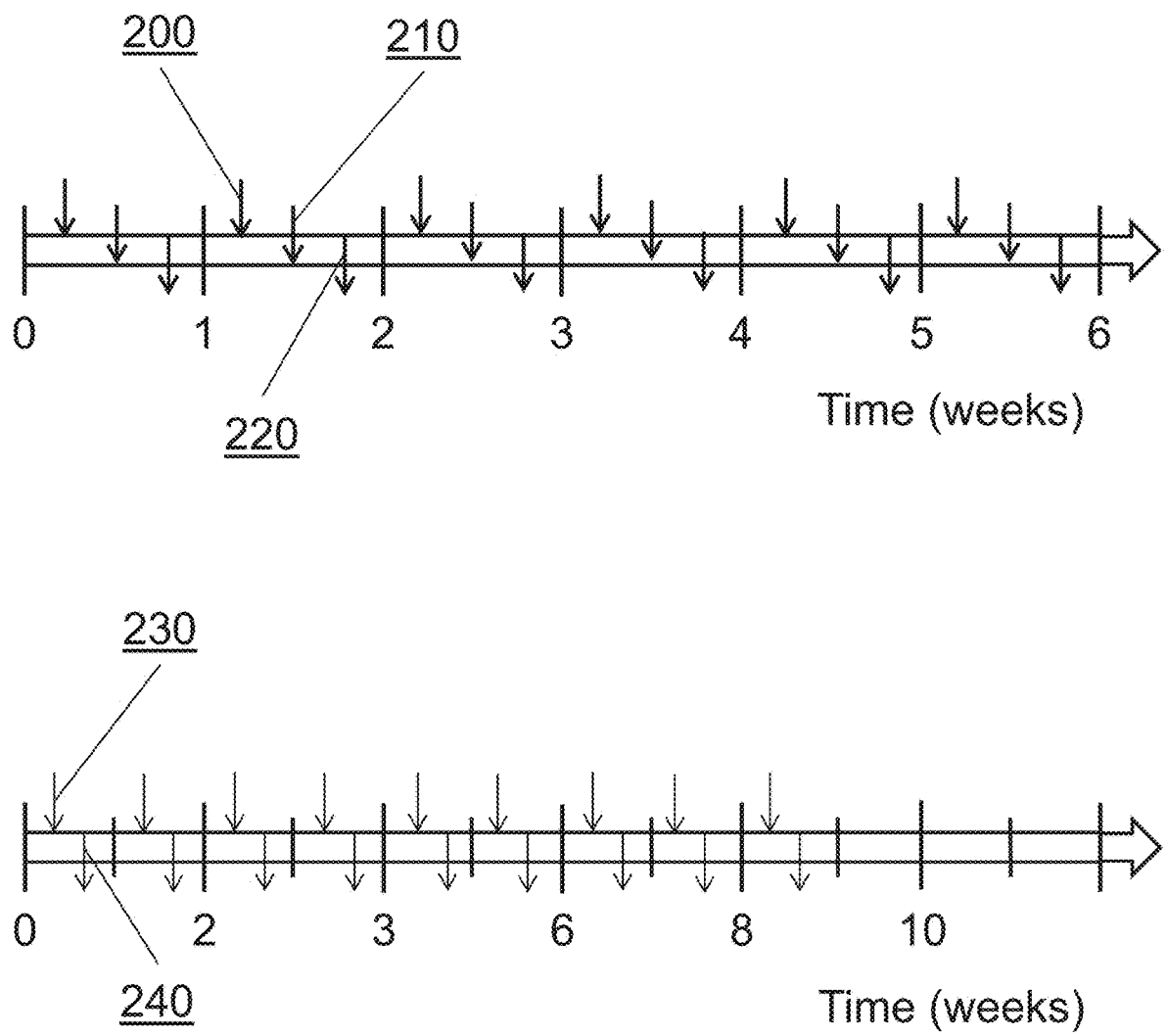
FIG. 10 illustrates the various time course laser light therapy treatment protocols employed over a many week period of therapeutic stimulation.

FIG. 9 shows an alternating square wave with a period of 200 milliseconds or 5 Hz (e.g. five (5) cycles per second), showing an indicative pulse rate frequency of 5 Hz and a duration of 200 milliseconds (even though the laser is off for half of the cycle it is included in the overall duration of a pulse rate frequency or pulse rate duration). The duration of treatment is shown to be from the start of the first waveform to the end of the last cycle. In FIG. 9, 3 cycles are shown for a total duration of treatment of 3 times 200 milliseconds or 600 milliseconds or 0.6 seconds. In clinical practice, the pulse rate frequency in Hz can range as discussed earlier. Various clinical protocols FIG. 10 illustrates the treatment protocol for three (3) times a week for six (6) weeks (upper time course) with 3 times a week treatments represented by arrows 200, 210 and 220 or for a two (2) times a week for nine (9) weeks clinical course of therapeutic cold laser therapy (lower time course) with twice a week treatments represented by arrows 230 and 240. The 3 times a week protocol for 6 weeks has strong clinical evidence regarding its effectiveness. The long but lower stimulation of ATP production encourages a longer period of enhanced cell function and repair. It also gives the body ample time to breakdown and reabsorb scar tissue. Increased ATP also allows for a longer period of neurogenesis. The more stimulation of synapse and neuronal activity the more connections will be established.

If the first course of therapy in not sufficient, a second round of 18 treatments can be administered. The amount of additional treatments is established by the results of the TONI-3 non-verbal cognitive function test and the over symptom changes evaluated by the patient and therapist.

An objective neurodiagnostic biosensor based feedback loop would enable and assist the clinician in effectively treating the damaged area more completely. Scattering causes lost time for the patient and the clinician by treating parts of the brain that may or may not need treatment. Over stimulation and under stimulation will no longer be a concern for the clinician when an objective biosensor based biomarker panel is used to guide therapy on a session by session, week by week or month by month basis, resulting in, a more controlled treatment with better results.

The use of LLLT to stimulate nerve regrowth and shut down pain sensors is well documented. The treatment of neuropathy and nerve damage has significant results with the decrease of sensitivity and pain level. The protocol is individual to the patient. However, using the spine as the main target for increasing ATP in nerve cells has been highly effective. The use of LED/Laser probe with continuous wave parameters is highly successful for destimulating pain responses in the spine. The use of LLLT increases the body's ability to regenerate nerve tissue by up to 300%.

Nervous System Aliments and Application of Cold Laser Light Therapy

The 9 point pattern delivered 3 times a week has shown to be effective in a host of neurological conditions. There is no indication to suggest the treatment will not continue to be the staple for treating all neurological conditions. The list of conditions treated over the last 9 years on over 2,000 patients suggests the 9 point protocol at 3 times a week with an 810 nm LED probe at 2.5 Hz pulse rate frequency, with a total treatment duration at each physical site for 1 minute is the corner stone for all present and future treatment protocols for neurological conditions.

Concussion (mTBI)—has a significant positive outcome when treated with LLLT and the 9 point protocol seen in FIG. 5. The typical treatment plan involving all 9 point protocols are 2-3 times per week. The protocols are every 48 hours during the week excluding weekends (ex. Monday, Wednesday, Friday), or every 72 hours excluding weekends (ex. Tuesday, Thursday).

Patients average over a 40% jump in their pre- and post-cognitive function test scores using the TONI-3 test. Patients treated by the inventors have experienced loss of concussed symptoms in as little as 24 hours. Patients notice a reduction in light and noise sensitivity, they are less frustrated, experience less foggy brain, better memory and attention skills. They have increased stamina for complex situations involving multiple conversations, and a high level of visual stimulation. They experience better sleep patterns, more rested sleep, higher energy levels and over all better feelings about life. The treated patients also experience lower levels of depression and increased libido. They have experienced a significant return of cognitive function.

Figure 11:
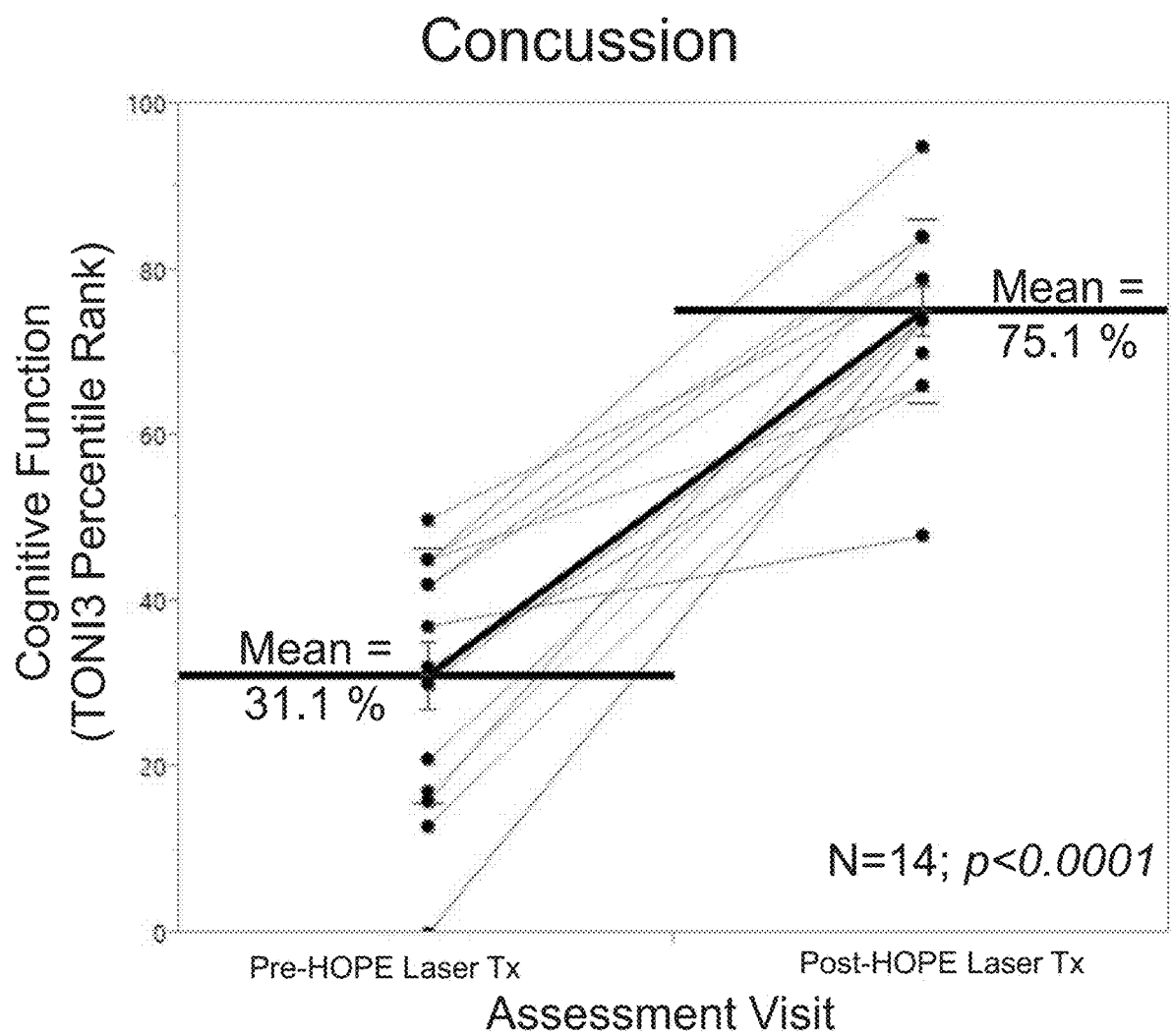
FIG. 11 is a graph showing the pre-treatment versus post-treatment results of cognitive performance on a cohort of concussion patients.

Concussed patients noticed a significant change within the first few treatments. Symptoms were less severe and had a significant decline in intensity and frequency of headaches. Sleep patterns stabilized and most patients reported a feeling of overall improvement and wellness. As shown in FIG. 11, the average patient scored a 31% on the TONI-3 test. The patients achieved a 44% increase on average with treatment. Comparing this gain to standard educational intervention, this increase would take approximately 4.5 years to achieve, as opposed to 6 to 12 weeks. An increase of more than 10% is considered a significant increase.

Mod-severe TBI—Millions of people are currently dealing with the side effects of TBI. Currently there are little to no treatment options to encourage neurogenesis and to increase cognitive function. Increasing both neurogenesis and cognitive function will assist the patient in achieving a more normal life style. The inventors have shown that a patient has a significant positive outcome when treated with LLLT and the 9 point protocol seen in FIG. 5 with the typical treatment plan involving all 9 point protocols 2-3 times per week. The protocols are every 48 hours during the week excluding weekends (ex. Monday, Wednesday, Friday), or every 72 hours excluding weekends (ex. Tuesday, Thursday). The laser treatment protocol is highly significant in its effect of many different conditions. The impact on healthcare costs could be staggering, less PT, home nurse care, medication use and doctor visits. This treatment protocol has shown to make significant strides like no other therapy available to date for patients with a variety of brain injuries or disorders.

Depression—Patients with depression—some of which were on high doses of medications—were treated using the treatment protocols described herein. One patient was on 15 different medications, which he has been able to lower since treatment to two medications, one of which is a sleeping aid. The basic 9 point pattern was used in all patients. The 9 point pattern has the ability to stimulate almost all areas of the brain resulting in major changes in cognitive function. If one can keep the results high with the same pattern it makes the process much more user friendly with a broad range of understanding for clinicians.

Alzheimer's disease—The treatment pattern for Alzheimer's disease has the basic 9 point pattern with two additional points added as shown in FIG. 6B. These two additional points help the stimulation of the frontal lobe. The laser probe is placed on the skull at a 30 degree angle on the inside of the bridge of the nose and the midline of the orbit. The angle allows the laser to reach higher into the frontal lobe without having to worry about penetration of the frontal bone of the skull.

Parkinson's disease—The treatment pattern for Parkinson disease has the basic 9 point pattern with two additional points added as shown in FIG. 6A. These two additional points help the stimulation of the parietal lobe. The parietal lobe manufactures the majority of dopamine in the brain. Although the laser therapy is scattered when it comes in contact with the bones of the skull, research suggests that the areas where the IR light is first introduced receives slightly more IR light. Stimulation of the parietal lobe will help increase the production of dopamine.

Duchene Muscular Dystrophy (DMD)—The treatment pattern for Duchene Muscular Dystrophy also has the basic 9 point pattern. The reintroduction of dystrophin back to the muscle has in treated patients allowed the muscles to recuperate and rebuild increasing strength and mobility. The patient had a 10% curvature of the spine correct itself after the conclusion of treatment.

Attention Deficit Hyperactivity Disorder (ADHD)—The learning disabilities, ADHD, ADD, Central Auditory Processing Disorder, Autism, Tourette's and a host of neurologically based learning disabilities have shown a significant increase in cognitive function when treated using the treatment protocols described herein. ADHD has a significant positive outcome when treated with LLLT and the 9 point protocol seen in FIG. 5. The typical treatment plan involving all 9 point protocols are 2-3 times per week. The protocols are every 48 hours during the week excluding weekends (ex. Monday, Wednesday, Friday), or every 72 hours excluding weekends (ex. Tuesday, Thursday).

Post-traumatic stress disorder—The treatment pattern for PTSD also has the basic 9 point pattern. This pattern has had significant change in PTSD patients, sleep patterns including nightmare, cognitive function, stamina, and cognitive function. PTSD has a significant positive outcome when treated with LLLT and the 9 point protocol seen in FIG. 5. The typical treatment plan involving all 9 point protocols are 2-3 times per week. The protocols are every 48 hours during the week excluding weekends (ex. Monday, Wednesday, Friday), or every 72 hours excluding weekends (ex. Tuesday, Thursday).

Stroke—The treatment pattern for Stroke is the basic 9 point pattern seen in FIG. 5. Increasing ATP, increased blood flow and decreased inflammation assist the brain in healing. The 36 treatment plan is performed 3 times a week for 12 weeks.

Neuropathy—The treatment pattern for neuropathy is the basic 9 point pattern seen in FIG. 5 and also has a significant positive outcome when treated with LLLT. Again, the laser protocols call for treatments 2-3 times per week. The treatment protocols are every 48 hours during the week excluding weekends (ex. Monday, Wednesday, Friday), or every 72 hours excluding weekends (ex. Tuesday, Thursday). The IR light has shown in studies to increase nerve regeneration by up to 300%. Neuropathy due to nerve damage can assist the body significantly in the healing of neuropathy.

Chronic Fatigue— Although there are many reasons for chronic fatigue, it appears that LLLT has the ability through increased cellular function to help alleviate the symptoms associated with chronic fatigue.

Down's Syndrome—Down's syndrome patients have been shown to have a positive outcome when treated with LLLT and the 9 point protocol seen in FIG. 5. The typical treatment plan involving all 9 point protocols are 2-3 times per week. The protocols are every 48 hours during the week excluding weekends (ex. Monday, Wednesday, Friday), or every 72 hours excluding weekends (ex. Tuesday, Thursday). The patient has seen increased cognitive function, increased fine motor function, increased in speech and task based understanding.

TABLE 1

Summary of some of the patients treated by the systems and methods of the present invention.

| Subject ID | Gender | 1ary. Indication | 2ndary. Indication | PreTax. % Rank | PostTax. % Rank | TONI3. % Rank. Change |
|---|---|---|---|---|---|---|
| HLI001 | M | Concussion | | 0 | 74 | 74 |
| HLI002 | M | Concussion | | 37 | 48 | 11 |
| HIL003 | M | Stroke | | 26 | 32 | 6 |
| HLI006 | M | Stroke | | 24 | 37 | 13 |
| HLI007 | F | Stroke | | 16 | 23 | 7 |
| HLI008 | M | Concussion | CAPD | 32 | 66 | 34 |
| HLI009 | F | Depression | | 13 | 79 | 66 |
| HLI010 | M | Tourettes | | 8 | 34 | 26 |
| HLI011 | M | Depression | | 45 | 58 | 13 |
| HLI012 | M | Alzheimer | | 19 | 26 | 7 |
| HLI015 | M | Autism | | 66 | 84 | 18 |
| HLI016 | M | Autism | | 12 | 45 | 33 |
| HLI017 | F | Concussion | | 21 | 74 | 53 |
| HLI021 | M | Learning disability | | 90 | 95 | 5 |
| HLI031 | F | Viral Encephalitis | | 2 | 5 | 3 |
| HLI032 | F | Concussion | ADHD | 42 | 79 | 37 |
| HLI033 | F | Concussion | | 30 | 74 | 44 |
| HLI035 | M | Parkinson | | 32 | 50 | 18 |
| HLI036 | M | Depression | Anxiety | 13 | 32 | 19 |
| HLI037 | M | Depression | | 34 | 58 | 24 |
| HLI041 | F | Concussion | | 17 | 74 | 57 |
| HLI042 | F | Concussion | | 17 | 74 | 57 |
| HLI043 | M | Concussion | | 50 | 79 | 29 |
| HLI045 | F | Concussion | | 45 | 84 | 68 |
| HLI047 | F | Lyme's Disease | | 39 | 74 | 35 |
| HLI048 | M | Depression | | 13 | 27 | 14 |
| HLI049 | M | Concussion | | 42 | 84 | 42 |
| HLI050 | M | Concussion | | 45 | 95 | 50 |
| HLI052 | F | Seizures | | 5 | 30 | 25 |
| HLI055 | F | Concussion | | 13 | 70 | 57 |
| HLIO56 | M | Stroke | | 32 | 74 | 42 |
| HLI057 | F | CAPD | | 94 | 99 | 5 |
| HLI058 | M | Concussion | | 45 | 66 | 21 |
| HLI059 | F | Depression | | 26 | 91 | 65 |

Other indications that could be treated by the system and methods of the present invention are discussed below. Prophetic indications that should be treatable by LLLT according to similar conditions or theories are the following non-limiting conditions: (1) Chronic Traumatic Encephalopathy (CTE)—The 9 point pattern has had success treating concussion and has notably reduced scar tissue. (2) Circulation Issues—The research states LLLT is a vaso-capillary dilator therefore increasing circulation assisting those with compromised circulator systems. (3) Cerebral Palsy—A disorder where blunt trauma to the brain occurs in vitro. The increased neuro-genesis and ATP should assist the brain in healing, especially in an infant which is already growing and producing neurons. (4) Lazy Eye—Amblyopia—This disorder is primarily muscular. LLLT has research and clinical data supporting its efficacy in effecting muscle tissue. (5) Mitochondrial Disorders—The increase of ATP in mitochondria which is duly noted in the research should be highly effective in treating mitochondrial disorders. (6) Behavioral Disorders—LLLT has significantly assisted in the regulations of neurological elements in other chemically deficient conditions. There is no scientific reason that suggests that LLLT would not be beneficial in the treatment of behavioral disorders, especially given its positive effects on ADHD and depression. (7) Lymphatic Issues—LLLT according to research increases the lymphatic system. There has been research in the reduction of lymphedema.

Examples

While the above description contains many specifics, these specifics should not be construed as limitations on the scope of the invention, but merely as exemplifications of the disclosed embodiments. Those skilled in the art will envision many other possible variations that are within the scope of the invention. The following examples will be helpful to enable one skilled in the art to make, use, and practice the present invention.

Example 1. Arrangement of the Hardware/Software Systems

The base laser unit 10 should be placed on a mobile cart or tray. The unit 10 is plugged into the electrical receptacle of a 110 volt 15 amp electrical socket. The laser probes 30 should be placed in the two ports on the right side of the unit 10. Usually a 69 or 104 LED probe and a Laser/LED probe should be available for use. The timer is set to 1 minute on the left side of the unit and the frequency is set to 2.5 Hz on the right side of the unit 10. The key is then placed in the control locking system and the unit 10 is turned on. The operator then waits for the calibration lights. Once the unit 10 beeps and lights up, the unit 10 is now ready to complete the entire treatment protocol. There is nothing else that needs to be done to the unit to finish treating the patient. The patient should be placed on a bed with a pillow or a chair that does not extend beyond the shoulder to keep the occipital portion of the brain and neck exposed. Since the object being treated (the brain) is spherical, the 69 cluster or laser with approximately 3" in diameter should be used.

Example 2. Applying the 9 Point Treatment Pattern to Concussion Patients

Using the methods described in Example 1, the inventors have now applied the LLLT to concussion patients.

To apply the light to the head using the 9 point pattern, the patient is inspected and instructed to remove any eyewear, hats, hair bands or large earrings. If the subject has thick hair, the hair is parted in order to get direct exposure to the skin. The laser probe 30 is placed on the center of the head (point 1 in FIG. 5). It is important to keep the laser as perpendicular to the center of the head as possible as the photons need to be delivered in a straight line, not on an angle. Once the laser has been properly placed, the button on the top of the probe 30 is pushed to start treatment. The on/off switch is a push button switch, meaning that it does not have to be held down, just push it and release. When the treatment is finished, the timer will automatically turn off the probe 30.

The laser probe 30 is then moved to the 2nd position as shown in FIG. 5. The 2nd point is located at the left side of the occipital and behind the left ear. It is important to note that the probe 30 needs to be placed so the edge of the probe 30 is slightly below the occipital ridge as it is undesirable for the IR light to pass into the neck instead of the brain. It is important to remember to keep the probe 30 directly on the skin and to hold the probe 30 perpendicular to the area being treated. The probe 30 should be pointing toward the opposite point of the brain toward point 3 in FIG. 5. Once the probe 30 is in position, the button is pushed and released and the probe 30 is held in position until the probe 30 shuts off after 1 minute of pulsed light therapy.

The operator next places the probe 30 at treatment point #3 in FIG. 5. The probe is placed on the right side of the skull approximately 2" down from the center point #1, and straight up from the center of the patient's ear. Once the probe 30 is in position, the button is pushed and released and the probe 30 is held in position until the probe 30 shuts off after 1 minute. The 4th treatment point is located at the right side of the occipital and behind the right ear. It is important to note the probe 30 needs to be placed so the edge of the probe is slightly below the occipital ridge for, as noted above, it is undesirable for the IR light to pass into the neck instead of the brain. The probe should be pointing toward the opposite point of the brain, i.e. toward point #5 in FIG. 5. Once the probe 30 is in position, the button is pushed and released and the probe 30 is held in position until the probe 30 shuts off.

The operator next proceeds to point #5 in FIG. 5. The probe 30 is placed on the left side of the skull approximately 2" down from the center point #1, and straight up from the center of the patient's left ear. Once the probe is in position, the button is pushed and released and the probe 30 is held in position until the probe 30 shuts off. The subject is instructed to close their eyes and to look away from the IR light until the completion of the treatment protocol.

Treatment point #6 is located on the left side of the forehead as shown in FIG. 5. The probe is placed so that the lower ridge of the probe 30 is laying on the top of the cheek bone and the front ridge of the probe 30 is adjacent to the edge of the eye lid. Care must be taken to ensure that the probe 30 is not shining light directly into any part of the eye. Once the probe 30 is in position, the button is again pressed and released and the probe is held perpendicular to the temple area. The operator should note that the patient will see the light through their eyelids. The probe should be positioned on the temporal bone not on the soft tissue of the eye.

Treatment point #7 is located above the center of the left eye on the forehead. Note the probe 30 should not be over any part of the soft tissue of the eye. The button is again pushed and released and the probe 30 is held perpendicular to the frontal bone until the probe timer turns off. Treatment point #8 is located above the center of the right eye on the forehead. Again, the probe 30 should not be over any part of the soft tissue of the eye. The button is again pushed and released and the probe is held perpendicular to the frontal bone until the probe timer turns off.

Point #9 is located on the right side of the forehead as shown in FIG. 5. The probe 30 is placed so that the lower ridge of the probe 30 is laying on the top of the cheek bone and front ridge of the probe 30 is adjacent to the edge of the eye lid. Care is again taken to ensure that the probe is not shining light directly in to any part of the eye. Once in position, the button is again pushed and released and the probe 30 is held perpendicular to the temple area. Patients have shown significant change in cognitive function through such a treatment protocol. Patients on average had a 44% increase in cognitive function. Some exhibited remarkable recovery of up to a 74% increase in cognitive function.

The above procedure was applied to N=14 concussion patients the results of which can be observed in the graphical FIG. 11 where one sees the pre-treatment cognitive performance for each individual as well as the post-treatment cognitive performance on the TONI-3 cognitive assessment test, an objective measure of cognitive performance. Each person is connected by a faint line while the cohort mean pre-treatment value is shown to be 31.1 percentile rank on the TONI-3. After treatment with the 3×/6 week 9 point treatment protocol of the present invention, the cohort mean percentile rank was 75.1%, a 44 percentile rank increase in just 6 weeks. The two cohort means are connected by a bold line. Typically, each decade of increase is associated with a year of standard therapy. Thus, the treatment protocol was able to do the equivalent of nearly 4 and half years in just 6 weeks.

Example 3. Applying the 9 Point Treatment Pattern to Depression Patients

Inspect the patient and have them remove any eyewear, hats, hair bands or large earrings. If the subject has thick hair, part the hair in order to get direct exposure to the skin. Place the laser probe 30 on the center of the head point 1 in FIG. 6A. It is important to keep the laser probe 30 as perpendicular to the center of the head as possible as the photons need to be delivered in a straight line, not on an angle. Once the laser probe 30 has been properly placed, push the button on the top of the probe 30 to start treatment. The on/off switch is a push button switch that may be just pushed and released. When the treatment is finished, the timer will automatically turn off the probe 30.

The laser probe 30 is moved to the 2nd position as shown in FIG. 6A. The 2nd point is located at the left side of the occipital and behind the left ear. It is important to note the probe needs to be placed so the edge of the probe is slightly below the occipital ridge as it is undesirable for IR light to pass into the neck instead of the brain. It is important to remember to keep the probe directly on the skin and to hold the probe perpendicular to the area being treated. The probe 30 should be pointing toward the opposite point of the brain toward treatment point #3 in FIG. 6A. Once the probe 30 is in position, push the button and release and hold the probe 30 in position until the probe 30 shuts off.

The laser probe 30 is moved to point #3 in FIG. 6A. Place the probe 30 on the right side of the skull approximately 2" down from the center point #1, and straight up from the center of the patient's ear. Once the probe 30 is in position, push the button and release and hold the probe in position until the probe 30 shuts off. The 4th treatment point is located at the right side of the occipital and behind the right ear. It is important to note the probe needs to be placed so the edge of the probe is slightly below the occipital ridge so as to prevent IR light from passing into the neck instead of the brain. The probe should be pointing toward the opposite point of the brain toward treatment point #5 in FIG. 5. Once the probe 30 is in position, push the button and release and hold the probe 30 in position until the probe 30 shuts off.

The operator next proceeds to treatment point #5 in FIG. 6A and places the probe 30 on the left side of the skull approximately 2" down from the center point #1, and straight up from the center of the patient's left ear. Once the probe 30 is in position, push the button and release and hold the probe 30 in position until the probe 30 shuts off. The subject is instructed to close their eyes and look away from the IR light until the completion of the treatment protocol.

Treatment point #6 is located on the left side of the forehead as shown in FIG. 6A. The probe 30 is placed so the lower ridge of the probe 30 is laying on the top of the cheek bone and front ridge of the probe 30 is adjacent to the edge of the eye lid. The operator ensures that the probe 30 is not shining light directly in to any part of the eye. Once in position, press the push button and release and hold the probe 30 perpendicular to the temple area. Since the patient will see the light through their eyelids, the probe 30 should be positioned on the temporal bone not on the soft tissue of the eye.

Treatment point #7 is located above the center of the left eye on the forehead. The probe 30 should be placed so as not to be over any part of the soft tissue of the eye. The button is pushed and released and the probe 30 is held perpendicular to the frontal bone until the probe timer turns off. Treatment point #8 is located above the center of the right eye on the forehead. As before, the probe 30 should not be over any part of the soft tissue of the eye. The operator pushes and releases the button and holds the probe 30 perpendicular to the frontal bone until the probe timer turns off.

Treatment point #9 is located on the right side of the forehead as shown in FIG. 6A. The probe 30 is placed so the lower ridge of the probe 30 is laying on the top of the cheek bone and front ridge of the probe 30 is adjacent to the edge of the eye lid such that the probe 30 does not shine light directly into any part of the eye. Once in position, the operator presses the push button and releases and holds the probe 30 perpendicular to the temple area. To prevent light from passing directly into the patient's eye, the probe 30 should be positioned on the temporal bone not on the soft tissue of the eye.

Figure 12:
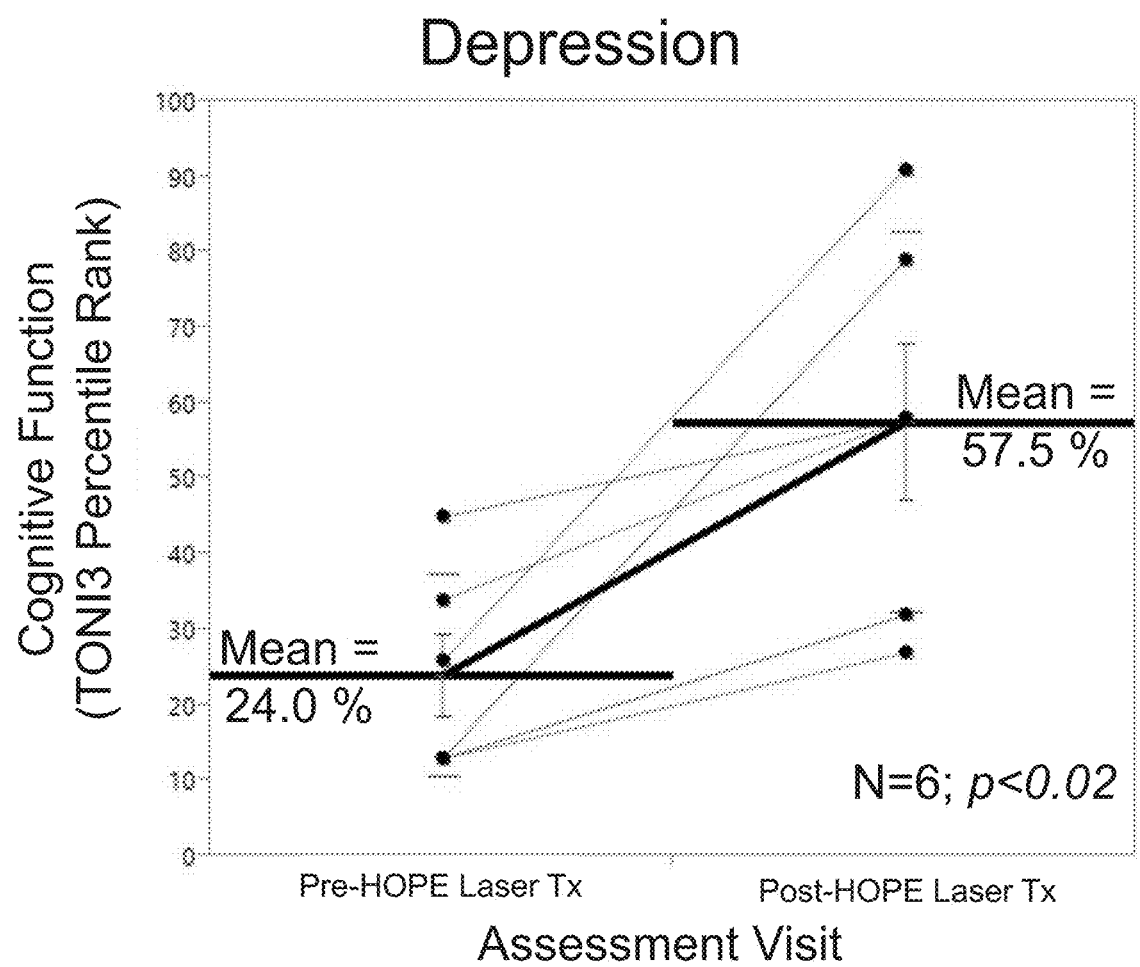
FIG. 12 is a graph showing the pre-treatment versus post-treatment results of cognitive performance on a cohort of depression patients.

The above procedure was applied to N=6 depression patients the results of which can be observed in the graphical FIG. 12 where one sees the pre-treatment cognitive performance for each individual as well as the post-treatment cognitive performance on the TONI-3 cognitive assessment test, an objective measure of cognitive performance. Each person is connected by a faint line while the cohort mean pre-treatment value is shown to be 24.0 percentile rank on the TONI-3. After treatment with the 3x/6 week 9 point treatment protocol of the present invention, the cohort mean percentile rank was 57.5%, a 33.5 percentile rank increase in just 6 weeks. The two cohort means are connected by a bold line. Typically, each decade of increase is associated with a year of standard therapy. Thus, the treatment protocol was able to do the equivalent of nearly 3 and one third years of treatment in just 6 weeks.

Example 4. Applying the 9 Point Treatment Pattern to a Stroke Patient

Inspect the patient and have them remove any eyewear, hats, hair bands or large earrings. If the subject has thick hair, part the hair in order to get direct exposure to the skin. Place the laser probe 30 on the center of the head point 1 in FIG. 5. It is important to keep the laser probe 30 as perpendicular to the center of the head as possible as the photons need to be delivered in a straight line, not on an angle. Once the laser probe 30 has been properly placed, push the button on the top of the probe 30 to start treatment. The on/off switch is a push button switch, meaning that the operator does not have to hold it down, just push it and release. When the treatment is finished, the timer will automatically turn off the probe 30.

The operator next moves the laser probe 30 to the 2nd position as shown in FIG. 5. The 2nd treatment point is located at the left side of the occipital and behind the left ear. It is important to note the probe 30 needs to be placed so the edge of the probe is slightly below the occipital ridge as it is undesirable for the IR light to pass into the neck instead of the brain. It is also important to remember to keep the probe 30 directly on the skin and to hold the probe 30 perpendicular to the area being treated. The probe 30 should be pointing toward the opposite point of the brain toward treatment point #3 in FIG. 5. Once the probe 30 is in position, the operator pushes the button and releases and holds the probe in position until the probe 30 shuts off.

The operator then proceeds to treatment point #3 in FIG. 5. The operator places the probe 30 on the right side of the skull approximately 2" down from the center point #1, and straight up from the center of the patient's ear. Once the probe 30 is in position, the operator pushes the button and releases and holds the probe 30 in position until the probe 30 shuts off. The 4th treatment point is located at the right side of the occipital and behind the right ear. It is again important to note the probe 30 needs to be placed so the edge of the probe 30 is slightly below the occipital ridge to prevent passing the IR light into the neck instead of the brain. The probe 30 should be pointing toward the opposite point of the brain toward treatment point #5 in FIG. 5. Once the probe 30 is in position, the operator pushes the button and releases and holds the probe 30 in position until the probe 30 shuts off.

The operator next proceeds to treatment point #5 in FIG. 5. The operator places the probe 30 on the left side of the skull approximately 2" down from the center point #1, and straight up from the center of the patient's left ear. Once the probe 30 is in position, the operator pushes the button and releases and holds the probe 30 in position until the probe 30 shuts off. The subject is instructed to close their eyes and look away from the IR light until the completion of the treatment protocol.

Treatment point #6 is located on the left side of the forehead as shown in FIG. 5. The operator places the probe 30 so the lower ridge of the probe 30 is laying on the top of the cheek bone and front ridge of the probe 30 is adjacent to the edge of the eye lid. The operator should take care to make sure the probe 30 does not shine light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye.

Treatment point #7 is located above the center of the left eye on the forehead. As before, the probe 30 should not be over any part of the soft tissue of the eye. The operator pushes the button and releases and holds the probe 30 perpendicular to the frontal bone until the probe timer turns off Treatment point #8 is located above the center of the right eye on the forehead. As before, the probe 30 should not be over any part of the soft tissue of the eye. The operator pushes the button and releases and holds the probe perpendicular to the frontal bone until the probe timer turns off.

Finally, treatment point #9 is located on the right side of the forehead as shown in FIG. 5. The operator places the probe 30 so that the lower ridge of the probe 30 is laying on the top of the cheek bone and front ridge of the probe 30 is adjacent to the edge of the eye lid. The operator makes sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye.

Figure 13:
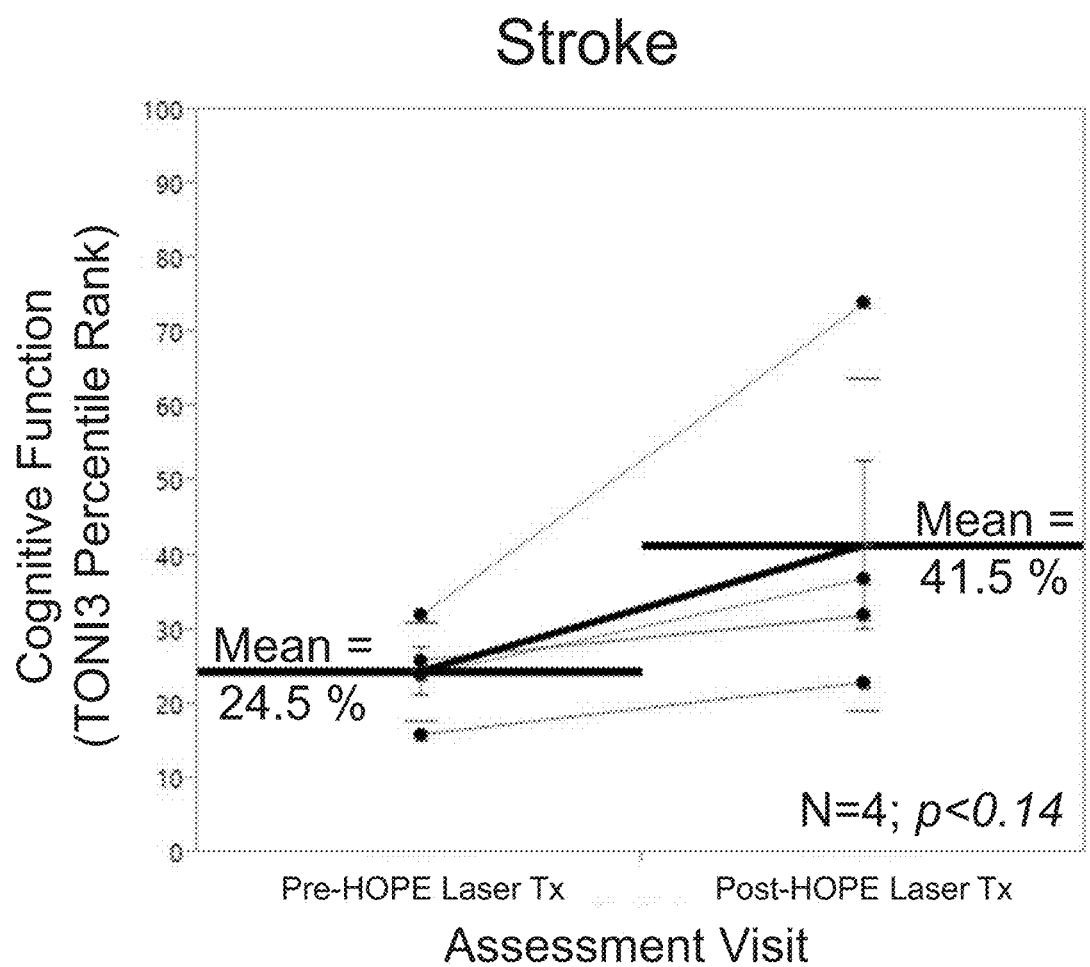
FIG. 13 is a graph showing the pre-treatment versus post-treatment results of cognitive performance on a cohort of stroke patients.

The above procedure was applied to N=4 depression patients, the results of which can be observed in the graphical FIG. 13 where one sees the pre-treatment cognitive performance for each individual as well as the post-treatment cognitive performance on the TONI-3 cognitive assessment test, an objective measure of cognitive performance. Each person is connected by a faint line while the cohort mean pre-treatment value is shown to be 24.5% percentile rank on the TONI-3. After treatment with the 3×/6 week 9 point treatment protocol of the present invention, the cohort mean percentile rank was 41.5%, a 17% percentile rank increase in just 6 weeks. The two cohort means are connected by a bold line. Typically, each decade of increase is associated with a year of standard therapy. Thus, the protocol was able to do the equivalent of nearly one and a half years of treatment in just 6 weeks.

Example 5. Applying the 9 Point Treatment Pattern to Other Indications

Before starting the treatment protocol, inspect the patient and have them remove any eyewear, hats, hair bands or large earrings. It the subject has thick hair, part the hair in order to get direct exposure to the skin. Place the laser probe 30 on the center of the head point 1 in FIG. 5. It is important to keep the laser probe 30 as perpendicular to the center of the head as possible as the photons need to be delivered in a straight line, not on an angle. Once the laser probe 30 has been properly placed, the operator pushes the button on the top of the probe 30 to start treatment. The on/off switch is a push button switch, so the operator does not have to hold it down, just push it and release. When the treatment is finished, the timer will automatically turn off the probe 30.

The laser probe 30 is next moved to the 2nd treatment position as shown in FIG. 5. The 2nd treatment point is located at the left side of the occipital and behind the left ear. It is important to note that the probe 30 needs to be placed so the edge of the probe 30 is slightly below the occipital ridge as it is undesirable for the IR light to shine into the neck instead of the brain. It is important to remember to keep the probe 30 directly on the skin and to hold the probe 30 perpendicular to the area being treated. The probe 30 should be pointing toward the opposite point of the brain toward treatment point #3 in FIG. 5. Once the probe 30 is in position, the operator pushes the button and releases and holds the probe 30 in position until the probe 30 shuts off.

The operator next proceeds to treatment point #3 in FIG. 5. The operator places the probe 30 on the right side of the skull approximately 2" down from the center point #1, and straight up from the center of the patient's ear. Once the probe 30 is in position, the operator pushes the button and releases and holds the probe 30 in position until the probe 30 shuts off. The 4th treatment point is located at the right side of the occipital and behind the right ear. It is important to note that the probe 30 needs to be placed so the edge of the probe 30 is slightly below the occipital ridge s it is undesirable for the IR light to shine into the neck instead of the brain. It is important to remember to keep the probe 30 directly on the skin and to hold the probe 30 perpendicular to the area being treated. The probe 30 should be pointing toward the opposite point of the brain toward treatment point #5 in FIG. 5. Once the probe 30 is in position, the operator pushes the button and releases and holds the probe 30 in position until the probe 30 shuts off.

Next, the operator proceeds to treatment point #5 in FIG. 5. The operator places the probe 30 on the left side of the skull approximately 2" down from the center point #1, and straight up from the center of the patient's left ear. Once the probe 30 is in position, the operator pushes the button and releases and holds the probe 30 in position until the probe 30 shuts off. The operator should remember to always keep the probe 30 perpendicular to the point of treatment and instruct the subject to close their eyes and look away from the IR light until the completion of the treatment protocol.

Treatment point #6 is located on the left side of the forehead as shown in FIG. 5. The operator places the probe 30 so that the lower ridge of the probe 30 is laying on the top of the cheek bone and front ridge of the probe 30 is adjacent to the edge of the eye lid. The operator should make sure the probe 30 is not shining light directly into any part of the eye. Once in position, the operator presses the push button and releases and holds the probe 30 perpendicular to the temple area. Since the patient will see the light through their eyelids, the probe should be positioned on the temporal bone and not on the soft tissue of the eye. Treatment point #7 is located above the center of the left eye on the forehead. As before, the probe 30 should not be over any part of the soft tissue of the eye. The operator pushes the button and releases and holds the probe 30 perpendicular to the frontal bone until the probe timer turns off.

Treatment point #8 is located above the center of the right eye on the forehead. The probe 30 should be placed so as not be over any part of the soft tissue of the eye. Once in place, the operator pushes the button and releases and holds the probe 30 perpendicular to the frontal bone until the probe timer turns off.

Treatment point #9 is located on the right side of the forehead as shown in FIG. 5. The operator places the probe 30 so that the lower ridge of the probe 30 is laying on the top of the cheek bone and front ridge of the probe 30 is adjacent to the edge of the eye lid. The operator should make sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone not on the soft tissue of the eye.

Example 6. Applying the 11 Point Treatment Pattern to a Parkinson Patient

Before starting the treatment protocol, the operator inspects the patient and has them remove any eyewear, hats, hair bands or large earrings. If the subject has thick hair, the subject parts the hair in order to get direct exposure to the skin. The operator places the laser probe 30 on the center of the head point 1 in FIG. 6A. It is important to keep the laser probe 30 as perpendicular to the center of the head as possible as the photons need to be delivered in a straight line, not on an angle. Once the probe has been properly placed, the operator pushes the button on the top of the probe 30 to start treatment. The on/off switch is a push button switch, so the operator does not have to hold it down, just push it and release. When the treatment is finished, the timer will automatically turn off the probe 30.

The operator then moves the probe 30 to the 2nd treatment point as shown in FIG. 6A. The 2nd treatment point is located at the left side of the occipital and behind the left ear. It is important to note that the probe 30 needs to be placed so that the edge of the probe 30 is slightly below the occipital ridge as it is undesirable to shine the IR light into the neck instead of the brain. It is also important to remember to keep the probe 30 directly on the skin and to hold the probe 30 perpendicular to the area being treated. The probe 30 should be pointing toward the opposite point of the brain toward treatment point #3 in FIG. 6A. Once the probe 30 is in position, the operator pushes the button and releases and holds the probe 30 in position until the probe 30 shuts off.

The operator next proceeds to treatment point #3 in FIG. 6A. The operator places the probe 30 on the right side of the skull approximately 2" down from the center point #1, and straight up from the center of the patient's ear. Once the probe 30 is in position, the operator pushes the button and releases and holds the probe 30 in position until the probe 30 shuts off. The 4th treatment point is located at the right side of the occipital and behind the right ear. It is important to note that the probe 30 needs to be placed so the edge of the probe 30 is slightly below the occipital ridge as it is undesirable to shine the IR light into the neck instead of the brain. It is also important to remember to keep the probe 30 directly on the skin and to hold the probe 30 perpendicular to the area being treated. The probe 30 should be pointing toward the opposite point of the brain toward treatment point #5 in FIG. 6A. Once the probe 30 is in position, the operator pushes the button and releases and holds the probe 30 in position until the probe 30 shuts off.

The operator next proceeds to treatment point #5 in FIG. 6A. The operator places the probe 30 on the left side of the skull approximately 2" down from the center point #1, and straight up from the center of the patient's left ear. Once the probe 30 is in position, the operator pushes the button and releases and holds the probe 30 in position until the probe 30 shuts off. The operator should remember to always keep the probe 30 perpendicular to the point of treatment and to instruct the subject to close their eyes and look away from the IR light until the completion of the treatment protocol.

Treatment point #6 is located on the left side of the forehead as shown in FIG. 6A. The operator places the probe 30 so that the lower ridge of the probe 30 is laying on the top of the cheek bone and front ridge of the probe is adjacent to the edge of the eye lid. The operator makes sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye.

Treatment point #7 is located above the center of the left eye on the forehead. The probe should be positioned so as not to cover any part of the soft tissue of the eye. The operator pushes the button and releases and holds the probe 30 perpendicular to the frontal bone until the probe timer turns off. Treatment point #8 is located above the center of the right eye on the forehead. As before, the probe 30 should not be over any part of the soft tissue of the eye. The operator pushes the button and releases and holds the probe perpendicular to the frontal bone until the probe timer turns off.

Treatment point #9 is located on the right side of the forehead as shown in FIG. 6A. The operator places the probe 30 so that the lower ridge of the probe 30 is laying on the top of the cheek bone and the front ridge of the probe 30 is adjacent to the edge of the eye lid. The operator makes sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye.

Treatment point #10 is located on the left side of the skull between point 1 and point 5 on FIG. 6A, approximately 1" towards the front of the skull. Once the probe 30 is in position, the operator pushes the button and releases and holds the probe 30 in position until the probe 30 shuts off. The operator should remember to always keep the probe 30 perpendicular to the point of treatment. Treatment point #11 is located on the right side of the skull between point 1 and point 3 on FIG. 6A, approximately 1" towards the front of the skull. Once the probe 30 is in position, the operator pushes the button and releases and holds the probe 30 in position until the probe 30 shuts off. Patients have seen a reduction in tremors, increased balance, stronger speech and more stamina under this treatment protocol.

Example 7. Applying the 11 Point Treatment Pattern to Alzheimer's Patients

Before starting the treatment protocol, the subject is inspected and is asked to remove any eyewear, hats, hair bands or large earrings. If the subject has thick hair, the hair is parted in order to get direct exposure to the skin. The operator places the laser probe 30 on the center of the head at treatment point #1 in FIG. 6B. It is important to keep the laser probe 30 as perpendicular to the center of the head as possible as the photons need to be delivered in a straight line, not on an angle. Once the probe 30 has been properly placed, the operator pushes the button on the top of the probe 30 to start treatment. The on/off switch is a push button switch so that the operator does not have to hold it down, just push it and release. When the treatment is finished, the timer will automatically turn off the probe 30.

The operator then moves the probe 30 to the 2nd treatment point as shown in FIG. 6B. The 2nd treatment point is located at the left side of the occipital and behind the left ear. It is important to note that the probe 30 needs to be placed so that the edge of the probe 30 is slightly below the occipital ridge as it is undesirable for the IR light to shine into the neck instead of the brain. It is also important to remember to keep the probe 30 directly on the skin and to hold the probe 30 perpendicular to the area being treated. The probe 30 should be pointing toward the opposite point of the brain toward treatment point #3 in FIG. 6B. Once the probe 30 is in position, the operator pushes the button and releases and holds the probe 30 in position until the probe 30 shuts off.

The operator next proceeds to treatment point #3 in FIG. 6B. The operator places the probe 30 on the right side of the skull approximately 2" down from the center point #1, and straight up from the center of the patient's ear. Once the probe 30 is in position, the operator pushes the button and releases and holds the probe 30 in position until the probe 30 shuts off. The 4th treatment point is located at the right side of the occipital and behind the right ear. It is important to note that the probe 30 needs to be placed so that the edge of the probe 30 is slightly below the occipital ridge as it is undesirable for the IR light to shine into the neck instead of the brain. It is also important to remember to keep the probe 30 directly on the skin and to hold the probe 30 perpendicular to the area being treated. The probe 30 should be pointing toward the opposite point of the brain toward treatment point #5 in FIG. 6B. Once the probe 30 is in position, the operator pushes the button and releases and holds the probe 30 in position until the probe 30 shuts off.

The operator next proceeds to treatment point #5 in FIG. 6B. The operator places the probe 30 on the left side of the skull approximately 2" down from the center point #1, and straight up from the center of the patient's left ear. Once the probe 30 is in position, the operator pushes the button and releases and holds the probe 30 in position until the probe 30 shuts off. The operator should remember to always keep the probe 30 perpendicular to the point of treatment and to instruct the subject to close their eyes and look away from the IR light until the completion of the treatment protocol.

Treatment point #6 is located on the left side of the forehead as shown in FIG. 6B. The operator places the probe 30 so that the lower ridge of the probe 30 is laying on the top of the cheek bone and the front ridge of the probe 30 is adjacent to the edge of the eye lid. The operator should make sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye. Treatment point #7 is located above the center of the left eye on the forehead. When properly placed, the probe 30 should not be over any part of the soft tissue of the eye. The operator pushes the button and releases and holds the probe 30 perpendicular to the frontal bone until the probe timer turns off.

Treatment point #8 is located above the center of the right eye on the forehead. As before, the probe 30 should not be over any part of the soft tissue of the eye. The operator pushes the button and releases and holds the probe 30 perpendicular to the frontal bone until the probe timer turns off Treatment point #9 is located on the right side of the forehead as shown in FIG. 6B. The operator places the probe 30 so that the lower ridge of the probe 30 is laying on the top of the cheek bone and the front ridge of the probe 30 is adjacent to the edge of the eye lid. The operator should make sure the probe 30 is not shining light directly into any part of the eye. Once in position, the operator presses the push button and releases and holds the probe 30 perpendicular to the temple area. Since the patient will see the light through their eyelids, the probe should be positioned on the temporal bone and not on the soft tissue of the eye.

Treatment point #10 is located on the left side of the skull between the bridge of the nose and the orbit or eye socket as shown in FIG. 6B. The operator places the LED/Laser probe 30 between the bridge of the nose and the eyeball. The subject should be reminded to close their eyes and look away from the IR light. The probe 30 should be angled toward the back of the skull on a 20 degree angle toward the top of the skull passing directly under treatment point #1, if one were to draw an imaginary line of projection. Once the probe 30 is in position, the operator pushes the button and releases and holds the probe in position until the probe 30 shuts off. The operator should remember to always keep the probe 30 perpendicular to the point of treatment.

Treatment point #11 is located on the right side of the skull between the bridge of the nose and the orbit or eye socket as shown in FIG. 6B. The operator places the LED/Laser probe 30 between the bridge of the nose and the eyeball. The subject should be reminded to close their eyes and to look away from the IR light. The probe 30 also should be angled toward the back of the skull on a 20 degree angle toward the top of the skull passing directly under treatment point #1, if one were to draw an imaginary line of projection. Once the probe 30 is in position, the operator pushes the button and releases and holds the probe 30 in position until the probe 30 shuts off. The operator should remember to always keep the probe 30 perpendicular to the point of treatment.

Example 8. Applying the 11 Point Treatment Pattern to Improve a Patient's Balance Prior to treatment, the operator should inspect the patient and have them remove any eyewear, hats, hair bands or large earrings. If the subject has thick hair, the subject should part the hair in order to get direct exposure to the skin. The operator places the laser probe 30 on the center of the head at treatment point #1 in FIG. 6C. It is important to keep the laser probe 30 as perpendicular to the center of the head as possible as the photons need to be delivered in a straight line, not on an angle. Once the laser probe 30 has been properly placed, the operator pushes the button on the top of the probe 30 to start treatment. The on/off switch is a push button switch, meaning that the operator does not have to hold it down, just push it and release. When the treatment is finished, the timer will automatically turn off the probe 30.

The operator next moves the laser probe 30 to the 2nd treatment position as shown in FIG. 6C. The 2nd treatment point is located at the left side of the occipital and behind the left ear. It is important to note that the probe 30 needs to be placed so that the edge of the probe 30 is slightly below the occipital ridge as it is undesirable to shine the IR light into the neck instead of the brain. It is also important to remember to keep the probe 30 directly on the skin and to hold the probe 30 perpendicular to the area being treated. The probe 30 should be pointing toward the opposite point of the brain toward treatment point #3 in FIG. 6C. Once the probe 30 is in position, the operator pushes the button and releases and holds the probe 30 in position until the probe 30 shuts off.

The operator then proceeds to treatment point #3 in FIG. 6C. The operator places the probe 30 on the right side of the skull approximately 2" down from the center point #1, and straight up from the center of the patient's ear. Once the probe 30 is in position, the operator pushes the button and releases and holds the probe 30 in position until the probe 30 shuts off. The 4th treatment point is located at the right side of the occipital and behind the right ear. It is important to note that the probe 30 needs to be placed so that the edge of the probe 30 is slightly below the occipital ridge as it is undesirable for the IR light to shine into the neck instead of the brain. It is also important to remember to keep the probe 30 directly on the skin and to hold the probe 30 perpendicular to the area being treated. The probe 30 should be pointing toward the opposite point of the brain toward treatment point #5 in FIG. 6C. Once the probe 30 is in position, the operator pushes the button and releases and holds the probe 30 in position until the probe 30 shuts off.

The operator then proceeds to treatment point #5 in FIG. 6C. The operator places the probe 30 on the left side of the skull approximately 2" down from the center point #1, and straight up from the center of the patient's left ear. Once the probe 30 is in position, the operator pushes the button and releases and holds the probe 30 in position until the probe 30 shuts off. The operator should remember to always keep the probe 30 perpendicular to the point of treatment and to instruct the subject to close their eyes and look away from the IR light until the completion of the treatment protocol.

Treatment point #6 is located on the left side of the forehead as shown in FIG. 6C. The operator places the probe 30 so that the lower ridge of the probe 30 is laying on the top of the cheek bone and the front ridge of the probe 30 is adjacent to the edge of the eye lid. The operator makes sure the probe 30 is not shining light directly into any part of the eye. Once in position, the operator presses the push button and releases and holds the probe 30 perpendicular to the temple area. Since the patient will see the light through their eyelids, the probe 30 should be positioned on the temporal bone and not on the soft tissue of the eye.

Treatment point #7 is located above the center of the left eye on the forehead. The probe 30 should be positioned so as not to be over any part of the soft tissue of the eye. The operator pushes the button and releases and holds the probe 30 perpendicular to the frontal bone until the probe timer turns off. Treatment point #8 is located above the center of the right eye on the forehead. As before, the probe should not be over any part of the soft tissue of the eye. The operator pushes the button and releases and holds the probe 30 perpendicular to the frontal bone until the probe timer turns off.

Treatment point #9 is located on the right side of the forehead as shown in FIG. 6C. The operator places the probe 30 so that the lower ridge of the probe 30 is laying on the top of the cheek bone and the front ridge of the probe 30 is adjacent to the edge of the eye lid. The operator makes sure the probe 30 is shining light directly into any part of the eye. Once in position, the operator presses the push button and releases and holds the probe 30 perpendicular to the temple area. Since the patient will see the light through their eyelids, the probe should be positioned on the temporal bone and not on the soft tissue of the eye.

Treatment point #10 is located at the base of the skull on the occipital ridge adjacent to the left side of the spine. The lower edge of the probe 30 should be on the occipital ridge and perpendicular to the skull pointing towards the frontal bone of the skull. Once in position, the operator presses the push button and releases and holds the probe perpendicular to the temple area. Treatment point #11 is located at the base of the skull on the occipital ridge adjacent to the right side of the spine. The lower edge of the probe 30 should be on the occipital ridge and perpendicular to the skull pointing towards the frontal bone of the skull. Once in position, the operator presses the push button and releases and holds the probe 30 perpendicular to the temple area. This protocol has shown great promise with balance issues. It has been shown that directing the IR light towards the cerebellum increases balance.

Those skilled in the art will appreciate that similar treatment protocols may be applied to subjects for the treatment of tinnitus using the probe placements illustrated in FIG. 7 and for tinnitus for TBI using the probe placements illustrated in FIG. 8. Also, similar treatment protocols may be applied to subjects for the treatment of glaucoma and low vision conditions caused from heart attack, stroke and any other neurological event that limits and compromises the optic nerve and the vision fields. The treatment locations and probe placements for these conditions also include the positions and variations of the treatment protocols described herein. These and other variations in the treatment protocols will be apparent to those skilled in the art in combination with the above teachings.

Those skilled in the art also will readily appreciate that many additional modifications and scenarios are possible in the exemplary embodiment without materially departing from the novel teachings and advantages of the invention. Accordingly, any such modifications are intended to be included within the scope of this invention as defined by the following exemplary claims.

What is claimed is:

1. A method of treating brain disease and/or brain injuries, comprising:

determining a treatment protocol for a subject having a particular brain disease and/or brain injury, said treatment protocol including a plurality of treatments, each treatment including application of light to the brain at a predetermined light frequency of 2.5 Hz. 10 Hz. or 1.25 kHz, and a predetermined duration of application of light, at respective positions in a pattern on the subject's skull in dependence upon the particular brain disease and/or brain injury being treated, wherein the treatment protocol comprises 18 treatments 3 times a week for 6 weeks or 2 times a week for 9 weeks on non-consecutive days, and wherein the treatment protocol is only to be used with a class 3 b laser or lower: and for each treatment, applying a light probe perpendicularly to the subject's skull at respective positions in the pattern that is predetermined to provide effective treatment for the particular brain disease and/or brain injury, and repeating application of light at said predetermined light frequency, for said predetermined duration of application of light, at each position, wherein the light probe is applied perpendicularly to each respective position on the subject's skull for about a minute to emit the light in a continuous mode or a pulsed mode, and the light from the light probe is in the form of an alternating square wave having a wavelength of 810 nm;

wherein the pattern comprises one of: a 9-point treatment pattern, an 11-point treatment pattern, and a 13-point treatment pattern, wherein in each treatment pattern, the light probe is adapted to move from one point to another point for treatment of each point, individually at a time.

2. The method of claim 1, wherein said pattern comprises the 9-point treatment pattern including a point on the center top of the subject's head, left and right side occipital positions behind the left and right ears, left and right sides of the skull straight up from a center of each ear of the subject, left and right sides of the forehead, and on the forehead above the left and right eyes, wherein the light probe is adapted to move from one point to another point for treatment of each point, individually at a time, in the 9-point treatment pattern.

3. The method of claim 1, wherein said pattern comprises the 9-point treatment pattern treatment pattern that is used in the treatment of concussion, traumatic brain injury, depression, Duchene Muscular Dystrophy, ADD, ADHD, central auditory processing disorder, autism, Tourette's syndrome, post-traumatic stress disorder, stroke, neuropathy, chronic fatigue, Down's syndrome, chronic traumatic encephalopathy, circulation, cerebral palsy, amblyopia, mitochondrial disorders, behavioral disorders, or lymphedema and conditions caused by external factors including vaccines and parasites.

4. The method of claim 1, wherein said pattern comprises the 11-point treatment pattern treatment pattern including a point on the center top of the subject's head, left and right side occipital positions behind the left and right ears, left and right sides of the skull straight up from a center of each ear of the subject, left and right sides of the forehead, on the forehead above the left and right eyes, and on the left and right sides of the skull between the point on the center top of the subject's head and points on the left and right sides of the skull straight up from the center of each ear of the subject, wherein the light probe is moved from one point to another point for treatment of each point, individually at a time, in the 11-point treatment pattern.

5. The method of claim 1, wherein said pattern comprises the 11-point pattern that is used in the treatment of Parkinson's disease.

6. The method of claim 1, wherein said pattern comprises the 11-point treatment pattern including a point on the center top of the subject's head, left and right side occipital positions behind the left and right ears, left and right sides of the skull straight up from a center of each ear of the subject, left and right sides of the forehead, on the forehead above the left and right eyes, and on the left and right sides of the skull between the bridge of the subject's nose and the orbit or eye socket, wherein the light probe is moved from one point to another point for treatment of each point, individually at a time, in the 11-point treatment pattern.

7. The method of claim 1, wherein said pattern comprises the 11-point treatment pattern is used in the treatment of Alzheimer's disease.

8. The method of claim 1, wherein said pattern comprises the 11-point treatment pattern including includes a point on the center top of the subject's head, left and right side occipital positions behind the left and right ears, left and right sides of the skull straight up from a center of each ear of the subject, left and right sides of the forehead, on the forehead above the left and right eyes, and at the base of the skull on the occipital ridge adjacent to the left and right sides of the spine, wherein the light probe is moved from one point to another point for treatment of each point, individually at a time, in the 11-point treatment pattern.

9. The method of claim 1, wherein said pattern comprises the 11-point treatment pattern that is used in the treatment of balance disorders.

10. The method of claim 1, wherein said pattern comprises the 11-point treatment pattern including a point on the center top of the subject's head, left and right side occipital positions behind the left and right ears, left and right sides of the skull straight up from a center of each ear of the subject, left and right sides of the forehead, on the forehead above the left and right eyes, and over the left and right ear canals, wherein the light probe is moved from one point to another point for treatment of each point, individually at a time, in the 11-point treatment pattern.

11. The method of claim 1, wherein said pattern comprises the 11-point treatment pattern that is used in the treatment of tinnitus.

12. The method of claim 1, wherein said pattern comprises the 13-point treatment pattern including a point on the center top of the subject's head, left and right side occipital positions behind the left and right ears, left and right sides of the skull straight up from a center of each ear of the subject, left and right sides of the forehead, on the forehead above the left and right eyes, over the left and right ear canals, and at the base of the skull on the occipital ridge adjacent to the left and right sides of the spine, wherein the light probe is moved from one point to another point for treatment of each point, individually at a time, in the 13-point treatment pattern.

13. The method of claim 1, wherein said pattern comprises the 13-point treatment pattern that is used in the treatment of tinnitus with traumatic brain injury.

* * * * *